United States Patent
Guidotti et al.

(10) Patent No.: US 12,004,737 B2
(45) Date of Patent: Jun. 11, 2024

(54) SUTURE FASTENERS

(71) Applicant: SV SWISSVORTEX LTD., Hunenberg (CH)

(72) Inventors: Andrea Guidotti, Zollikon (CH); Idan Tobis, Beth Hashmonai (IL); Georgios Stefopoulos, Zurich (CH)

(73) Assignee: SV SWISSVORTEX LTD., Hunenberg (CH)

( * ) Notice: Subject to any disclaimer, the term of this patent is extended or adjusted under 35 U.S.C. 154(b) by 599 days.

(21) Appl. No.: 16/967,999

(22) PCT Filed: Feb. 26, 2019

(86) PCT No.: PCT/IB2019/051517
§ 371 (c)(1),
(2) Date: Aug. 6, 2020

(87) PCT Pub. No.: WO2019/162923
PCT Pub. Date: Aug. 29, 2019

(65) Prior Publication Data
US 2021/0393258 A1    Dec. 23, 2021

Related U.S. Application Data

(60) Provisional application No. 62/635,156, filed on Feb. 26, 2018.

(51) Int. Cl.
*A61B 17/04*    (2006.01)
(52) U.S. Cl.
CPC ...... *A61B 17/0487* (2013.01); *A61B 17/0467* (2013.01); *A61B 2017/0488* (2013.01)
(58) Field of Classification Search
CPC combination set(s) only.
See application file for complete search history.

(56) References Cited

U.S. PATENT DOCUMENTS

| | | |
|---|---|---|
| 5,643,289 A | 7/1997 | Sauer et al. |
| 5,681,351 A | 10/1997 | Jamiolkowski et al. |
| (Continued) | | |

FOREIGN PATENT DOCUMENTS

| | | |
|---|---|---|
| WO | 2001/046537 | 6/2001 |
| WO | 2014/011794 | 1/2014 |
| WO | 2014/078237 | 5/2014 |

OTHER PUBLICATIONS

An International Search Report and a Written Opinion both dated Jun. 18, 2019, which issued during the prosecution of Applicant's PCT/IB2019/051517.
(Continued)

*Primary Examiner* — Sarah W Aleman
*Assistant Examiner* — Rachel S Highland
(74) *Attorney, Agent, or Firm* — Sughrue Mion, PLLC

(57) ABSTRACT

A surgical fastener instrument (30) includes an outer delivery tube (36); an inner delivery shaft (42), disposed at least partially in the outer delivery tube (36); and a handle (44) coupled to a proximal portion (46) of the outer delivery tube (36), and including a user control element (48) arranged to rotate the inner delivery shaft (42) with respect to the outer delivery tube (36). A suture fastener (32) is removably disposed in the outer delivery tube (36) in an unlocked conical helical configuration. Distal advancement of the inner delivery shaft (42), when one or more portions of one or more sutures (22) pass through respective portions of the suture fastener (32), transitions the suture fastener (32) from the unlocked configuration to a locked planar spiral configuration, in which the one or more sutures (22) are fixedly coupled to the suture fastener (32). Other embodiments are also described.

22 Claims, 21 Drawing Sheets

(56) References Cited

U.S. PATENT DOCUMENTS

| | | |
|---|---|---|
| 5,735,877 A | 4/1998 | Pagedas |
| 6,099,553 A | 8/2000 | Hart et al. |
| 6,355,050 B1 | 3/2002 | Andreas et al. |
| 6,358,258 B1 | 3/2002 | Arcia et al. |
| 6,402,765 B1 | 6/2002 | Monassevitch et al. |
| 6,409,743 B1 | 6/2002 | Fenton, Jr. |
| 7,094,247 B2 | 8/2006 | Monassevitch et al. |
| 7,335,221 B2 | 2/2008 | Collier et al. |
| 8,961,594 B2 | 2/2015 | Maisano et al. |
| 9,017,347 B2 | 4/2015 | Oba et al. |
| 9,055,939 B2 | 6/2015 | Fujisaki et al. |
| 9,078,645 B2 | 7/2015 | Conklin et al. |
| 9,801,719 B2 | 10/2017 | Miraki |
| RE47,209 E | 1/2019 | Jafari et al. |
| 2002/0077631 A1 | 6/2002 | Lubbers et al. |
| 2005/0149120 A1 | 7/2005 | Collier et al. |
| 2007/0083235 A1 | 4/2007 | Jervis et al. |
| 2007/0225736 A1 | 9/2007 | Zeiner et al. |
| 2007/0276437 A1 | 11/2007 | Call et al. |
| 2008/0228201 A1 | 9/2008 | Zarbatany et al. |
| 2008/0249545 A1 | 10/2008 | Shikhman |
| 2008/0281356 A1 | 11/2008 | Chau et al. |
| 2009/0112052 A1 | 4/2009 | Lund et al. |
| 2012/0158053 A1 | 6/2012 | Paulos |
| 2012/0160896 A1* | 6/2012 | Houard .............. A61B 17/068 227/179.1 |
| 2012/0283749 A1 | 11/2012 | Sauer |
| 2013/0231701 A1 | 9/2013 | Voss et al. |
| 2014/0031864 A1 | 1/2014 | Jafari et al. |
| 2014/0276979 A1 | 9/2014 | Sauer et al. |
| 2015/0366556 A1 | 12/2015 | Khairkhahan et al. |
| 2016/0007986 A1 | 1/2016 | Sauer |
| 2016/0270776 A1* | 9/2016 | Miraki .............. A61B 17/0487 |
| 2017/0049435 A1 | 2/2017 | Sauer et al. |
| 2017/0156720 A1 | 6/2017 | Moehle et al. |
| 2018/0070938 A1 | 3/2018 | Sauer |

OTHER PUBLICATIONS

An English translation of an Office Action dated Feb. 2, 2021 which issued during the prosecution of Japanese Patent Application No. 560253-2020.

Gao C et al., "Robotically assisted mitral valve replacement," J Thorac Cardiovasc Surg Apr. 2012; 143:S64-7.

Navarra E et al., "Robotic mitral valve repair: a European single-centre experience," Interact Cardio Vasc Thorac Surg Mar. 2017;25:62-7.

Efird JT et al., "Conditional long-term survival following minimally invasive robotic mitral valve repair: a health services perspective," Ann Cardiothorac Surg. Sep. 2015;4(5):433-42.

COR-KNOT ® MIS Technology Guide Aug. 2017.

Seco M et al., "Systematic review of robotic minimally invasive mitral valve surgery," Ann Cardiothorac Surg Nov. 2013;2(6):704-716.

Grapow MTR et al., "Automated fastener versus manually tied knots in minimally invasive mitral valve repair: impact on operation time and shortterm results," Journal of Cardiothoracic Surgery (Nov. 2015) 10:146.

U.S. Appl. No. 62/635,156, filed Feb. 26, 2018.

Extended European Search Report dated Nov. 10, 2021 from the European Patent Office in EP Application No. 21186406.1.

Office Action dated Jan. 19, 2023 in Chinese Application No. 201980014435.2.

* cited by examiner

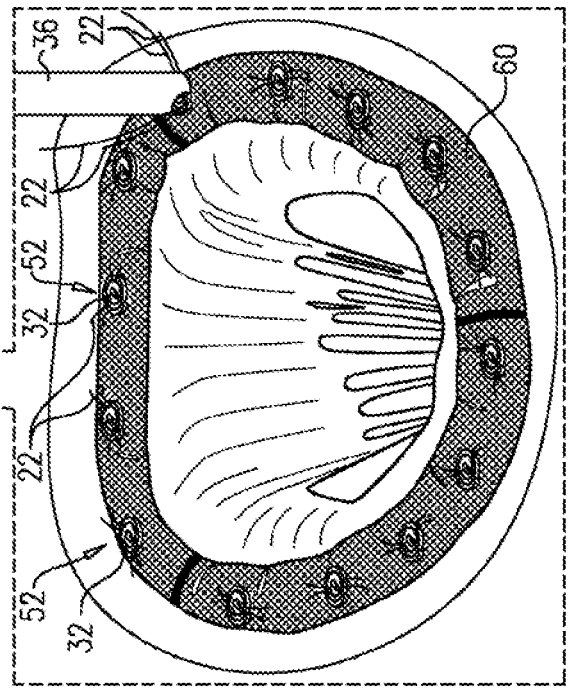
FIG. 5A
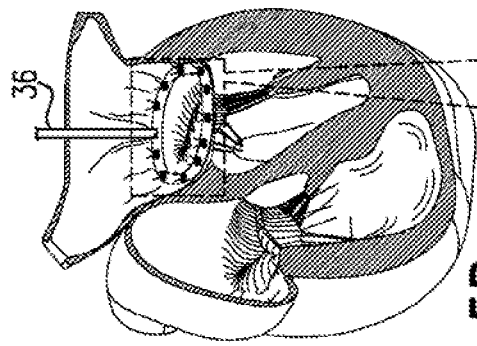
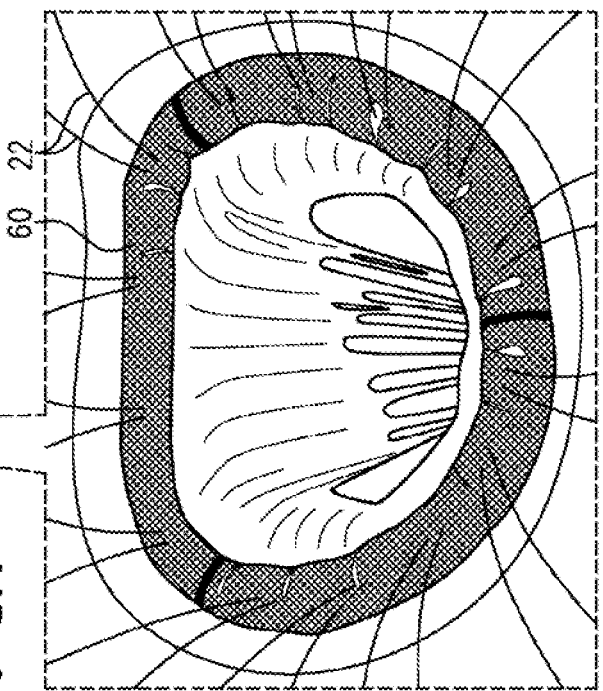
FIG. 5B
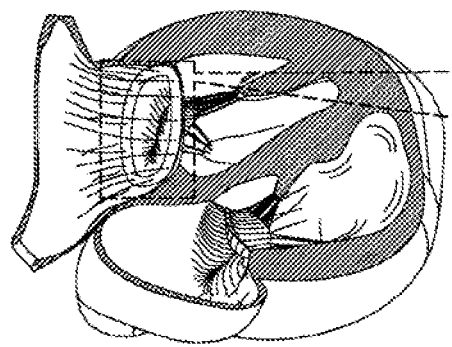

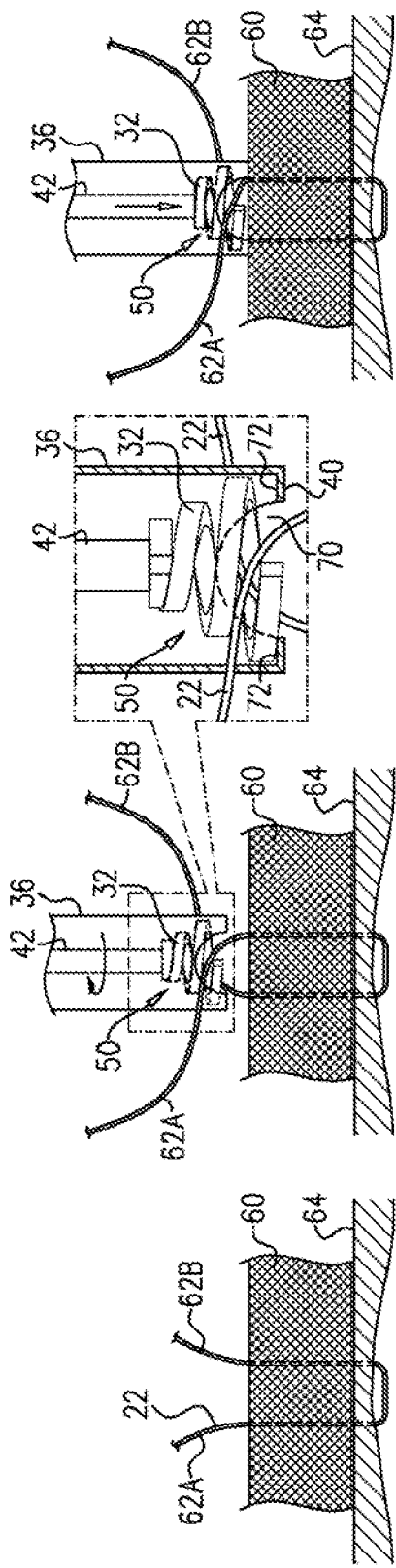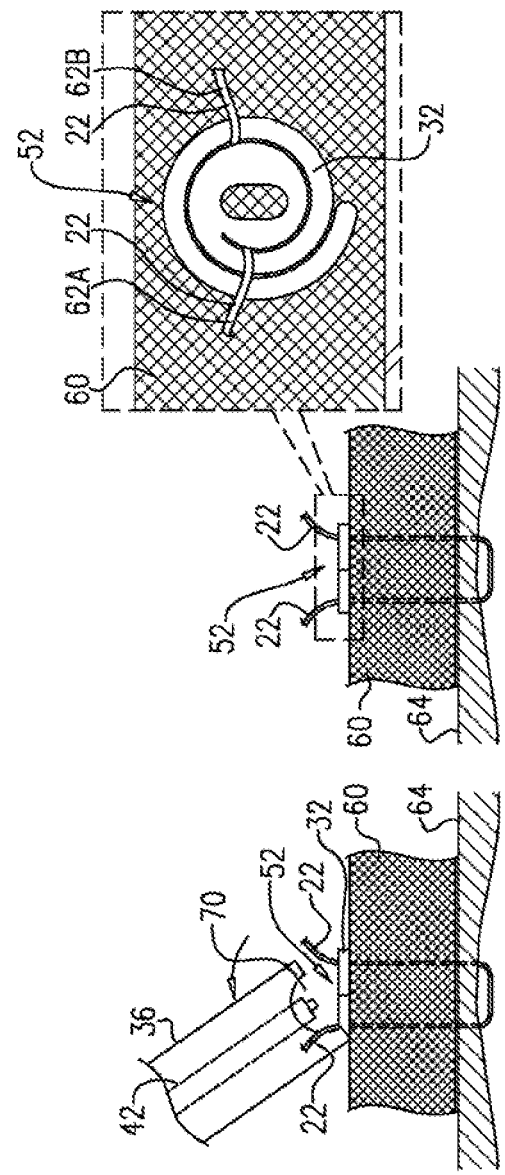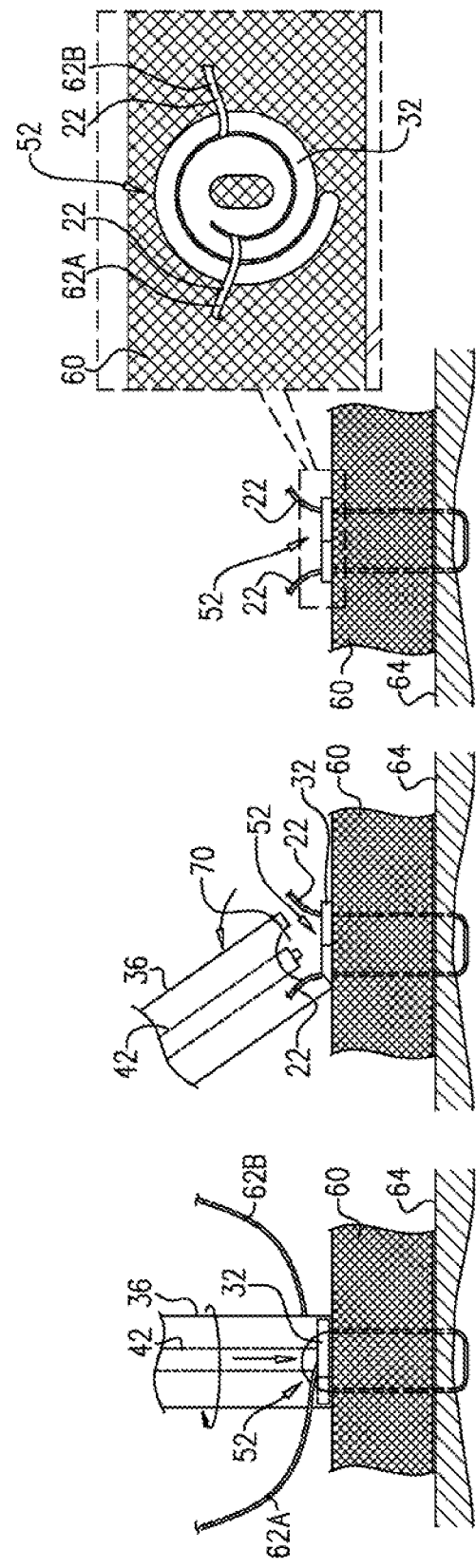

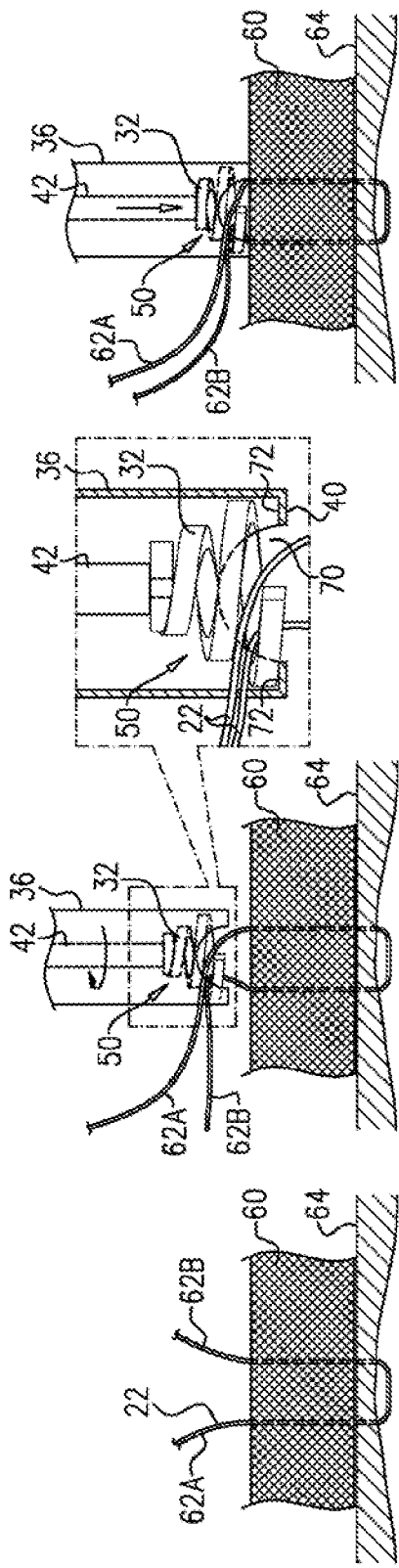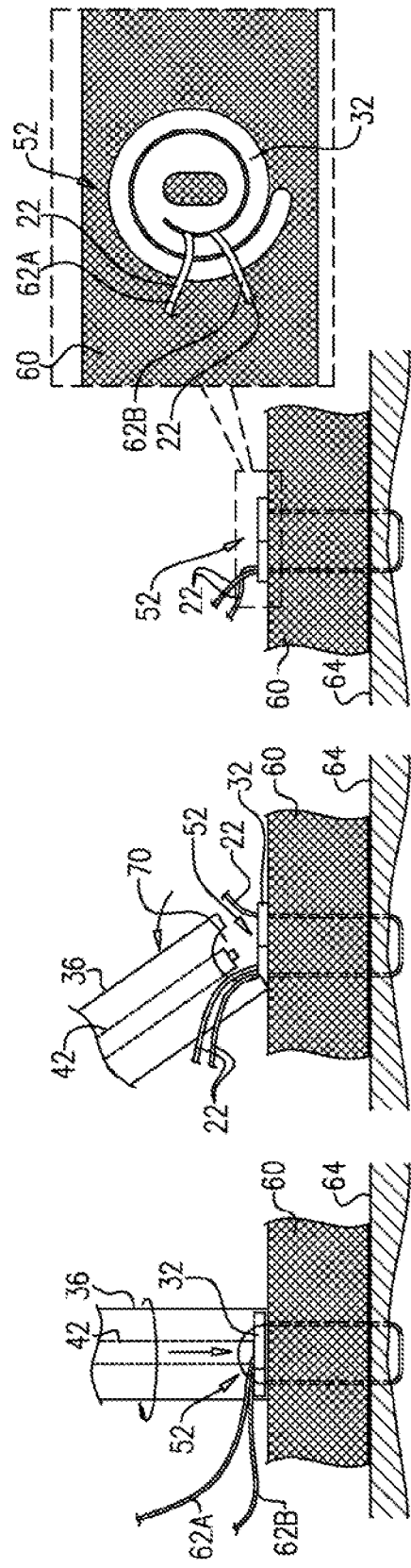

SUTURE FASTENERS

CROSS-REFERENCE TO RELATED APPLICATIONS

The present application is the U.S. national stage of International Application PCT/IB2019/051517, filed Feb. 26, 2019, which claims priority from U.S. Provisional Application 62/635,156, filed Feb. 26, 2018, which is assigned to the assignee of the present application and incorporated herein by reference.

FIELD OF THE APPLICATION

The present invention relates generally to surgical tools, and specifically to surgical suture fasteners.

BACKGROUND OF THE APPLICATION

The current standard of care treatment for heart valve disease is open-heart surgery, in which the valvular problem is corrected either by repair of the valve or replacement of the valve, with the use of therapeutic prostheses. These prostheses are held in position with respect to the cardiovascular tissue using sutures. These sutures are usually manually tied using hands or traditional knot pushers.

Recently, automated fastener devices have been developed. These devices exhibit safe, reliable and fast application, in combination with substantial time savings in cardioplegic arrest and cardiopulmonary bypass.

Cor-Knot® (LSI Solutions, Inc., Victor, NY, USA) is an automated titanium fastener indicated in the approximation of soft tissue and prosthetic materials, used in conjunction with either 2-0 polyester or 2-0/3-0 polypropylene sutures.

SUMMARY OF THE APPLICATION

Embodiments of the present invention provide a suture fastener system for fastening sutures in medical applications. The suture fastener system is typically used for automatic suture fastening for securing an implantable prosthesis to tissue of a patient, such as cardiac tissue, or for securing two or more cardiovascular tissues sutured together, e.g., for cardiac bypass surgery or anastomosis. The suture fastener system may be configured for use during open, minimally-invasive, percutaneous, laparoscopic, robotic, or other surgical procedures.

The surgical fastener system comprises a surgical fastener instrument and a suture fastener, typically a plurality of suture fasteners. The surgical fastener instrument typically comprises an outer delivery tube, which has a distal opening at a distal end of the outer delivery tube; an inner delivery shaft, which is disposed at least partially in the outer delivery tube; and a handle, which is coupled to a proximal portion of the outer delivery tube, and comprises a user control element arranged to rotate the inner delivery shaft with respect to the outer delivery tube.

The suture fastener is removably disposed in the outer delivery tube in an unlocked conical helical configuration. The surgical fastener instrument is arranged such that distal advancement of the inner delivery shaft, when one or more portions of the one or more sutures pass through respective portions of the suture fastener, transitions the suture fastener from the unlocked conical helical configuration to a locked planar spiral configuration, in which the one or more sutures are fixedly coupled to the suture fastener. The suture fastener can be fastened to the one or more sutures and any locations along the one or more sutures. This crimping of the suture fastener to the one or more sutures tightens the sutures and keeps them in place. This crimping of the suture fastener may replace standard suture knots, which are generally made manually by surgeons.

For some applications, the surgical fastener instrument is configured such that when the suture fastener is removably disposed in the outer delivery tube in the unlocked conical helical configuration, and the one or more sutures are disposed partially within the outer delivery tube, rotation of the inner delivery shaft rotates the suture fastener, thereby causing the one or more portions of the one or more sutures to pass through and become entangled in the respective portions of the suture fastener. This rotational technique for introducing the one or more sutures into the fastener obviates the need to hook the sutures or use a loop system to engage the sutures. The open shape of the suture fastener when in the unlocked conical helical configuration enables this rotational introduction technique.

The suture fastener may be used with many types of sutures, including monofilament sutures (e.g., comprising Prolete® Polypropylene Sutures (Ethicon US, LLC) of any diameter, because the suture fastener can apply sufficient friction to tightly grasp monofilament sutures between the turns of the planar spiral of the fastener.

If necessary, before the suture fastener has been crimped by the distal advancement of the inner delivery shaft, the one or more sutures can be released from the suture fastener by counter-rotation of the inner delivery shaft. This enables the repositioning of the surgical fastener instrument over the same one or more sutures in a different position or under different conditions (e.g., different tension). After the suture fastener has been crimped, the one or more sutures can be freed from the surgical fastener instrument by cutting the one or more sutures using (a) a scalpel in supra fastener position, (b) one or more blades of the surgical fastener instrument, which may be activated by a user control element of a handle of the surgical fastener instrument, without risking to damage the prosthesis to which the sutures are coupled, or (c) one or more blades defined by the suture fastener itself.

There is therefore provided, in accordance with an Inventive concept 1 of the present invention, a surgical fastener system for fastening one or more sutures, the surgical fastener system including:
(a) a surgical fastener instrument, which includes:
an outer delivery tube, which has a distal opening at a distal end of the outer delivery tube;
an inner delivery shaft, which is disposed at least partially in the outer delivery tube; and
a handle, which is coupled to a proximal portion of the outer delivery tube, and includes a user control element arranged to rotate the inner delivery shaft with respect to the outer delivery tube; and
(b) a suture fastener, which is removably disposed in the outer delivery tube in an unlocked conical helical configuration,
wherein the surgical fastener instrument is arranged such that distal advancement of the inner delivery shaft, when one or more portions of the one or more sutures pass through respective portions of the suture fastener, transitions the suture fastener from the unlocked conical helical configuration to a locked planar spiral configuration, in which the one or more sutures are fixedly coupled to the suture fastener.

Inventive concept 2. The surgical fastener system according to Inventive concept 1, wherein the suture fastener is configured to assume the unlocked conical helical configuration when in a resting state, and wherein the surgical fastener instrument is arranged such that the distal advancement of the inner delivery shaft transitions the suture fastener from the unlocked conical helical configuration to the locked planar spiral configuration by axially plastically deforming the suture fastener.

Inventive concept 3. The surgical fastener system according to Inventive concept 1, wherein a height of the suture fastener, when in the locked planar spiral configuration, is less than 5 mm.

Inventive concept 4. The surgical fastener system according to Inventive concept 1, wherein, when the suture fastener is in the locked planar spiral configuration, a height of the suture fastener is less than 25% of a greatest dimension of the suture fastener.

Inventive concept 5. The surgical fastener system according to Inventive concept 1, wherein the surgical fastener instrument further includes one or more blades, which are configured to cut the one or more sutures.

Inventive concept 6. The surgical fastener system according to Inventive concept 1, wherein the suture fastener is shaped as a double helix in the unlocked conical helical configuration, and a double planar spiral in the locked planar spiral configuration.

Inventive concept 7. The surgical fastener system according to any one of Inventive concepts 1-6.
- wherein the user control element is a first user control element, and
- wherein the handle includes a second user control element, which is arranged to cause the distal advancement of the inner delivery shaft.

Inventive concept 8. The surgical fastener system according to Inventive concept 7,
- wherein the surgical fastener instrument further includes one or more blades, which are configured to cut the one or more sutures, and
- wherein the second user control element is arranged to cause the distal advancement of the inner delivery shaft, and thereafter to cause the one or more blades to cut the one or more sutures.

Inventive concept 9. The surgical fastener system according to any one of Inventive concepts 1-6, wherein the user control element is arranged to both rotate the inner delivery shaft with respect to the outer delivery tube and to cause the distal advancement of the inner delivery shaft.

Inventive concept 10. The surgical fastener system according to Inventive concept 9, wherein the user control element is arranged to begin causing the distal advancement of the inner delivery shaft after beginning rotating of the inner delivery shaft.

Inventive concept 11. The surgical fastener system according to Inventive concept 10, wherein the user control element is arranged to begin causing the distal advancement of the inner delivery shaft after completing rotating of the inner delivery shaft.

Inventive concept 12. The surgical fastener system according to any one of Inventive concepts 1-6, wherein the surgical fastener instrument is arranged such that the distal advancement of the inner delivery shaft transitions the suture fastener from the unlocked conical helical configuration to the locked planar spiral configuration while the suture fastener is disposed entirely within the outer delivery tube.

Inventive concept 13. The surgical fastener system according to Inventive concept 12, wherein the distal end of the outer delivery tube is shaped so as to define one or more radially-inwardly-extending lips, each of which extends partially around the distal opening, and which hold the suture fastener in the outer delivery tube during distal advancement of the inner delivery shaft to transition the suture fastener from the unlocked conical helical configuration to the locked planar spiral configuration.

Inventive concept 14. The surgical fastener system according to any one of Inventive concepts 1-6, wherein the outer delivery tube is shaped so as to define one or more lateral openings that extend to the distal end, and facilitate insertion of the one or more portions of the one or more sutures into the outer delivery tube and through the respective portions of the suture fastener.

Inventive concept 15. The surgical fastener system according to Inventive concept 14, wherein the surgical fastener instrument is configured such that when the suture fastener is removably disposed in the outer delivery tube in the unlocked conical helical configuration, and the one or more sutures are disposed partially within the outer delivery tube:
rotation of the inner delivery shaft rotates the suture fastener, thereby causing the one or more portions of the one or more sutures to pass through the respective portions of the suture fastener.

Inventive concept 16. The surgical fastener system according to Inventive concept 15, wherein the surgical fastener instrument is configured such that the rotation of the inner delivery shaft rotates the suture fastener, thereby causing the one or more portions of the one or more sutures to become entangled with the respective portions of the suture fastener.

Inventive concept 17. The surgical fastener system according to any one of Inventive concepts 1-6, wherein the distal end of the outer delivery tube is shaped to allow distal passage of the suture fastener out of the distal opening when the suture fastener is in the locked planar spiral configuration.

Inventive concept 18. The surgical fastener system according to Inventive concept 17, wherein the distal end of the outer delivery tube is shaped to allow the distal release of the suture fastener out of the distal opening upon rotation of the outer delivery tube with respect to the suture fastener when the suture fastener is in the locked planar spiral configuration.

Inventive concept 19. The surgical fastener system according to any one of Inventive concepts 1-6,
- wherein the suture fastener is shaped so as to define a spiral portion, which is (a) conically helical when the suture fastener is in the unlocked conical helical configuration and (b) planar spiral when the suture fastener is in the planar spiral configuration, and
- wherein the suture fastener is shaped so as to define a radially-inward portion that, both when the suture fastener is in the unlocked conical helical configuration and when the suture fastener is in the locked planar spiral configuration, (a) is neither helical nor spiral, and (b) is disposed radially inward from the spiral portion.

Inventive concept 20. The surgical fastener system according to Inventive concept 19,
- wherein the radially-inward portion is shaped so as to define a non-circular and non-spiral opening, and
- wherein a distal end of the inner delivery shaft is shaped so as to engage the non-circular and non-spiral opening.

Inventive concept 21. The surgical fastener system according to Inventive concept 19, wherein an area of an upper surface of the radially-inward portion is between 5% and 15% of a total area of an upper surface of the suture fastener, including the radially-inward portion and the spiral portion.

Inventive concept 22. The surgical fastener system according to any one of Inventive concepts 1-6, wherein the surgical fastener system includes a plurality of suture fasteners, which are removably disposed in the outer delivery tube, each in an unlocked conical helical configuration.

Inventive concept 23. The surgical fastener system according to any one of Inventive concepts 1-6, further including sterile packaging, in which the suture fastener is removably disposed.

There is further provided, in accordance with an Inventive concept 24 of the present invention, a suture fastener for fastening one or more sutures, the suture fastener shaped so as to define:
- a spiral portion; and
- a radially-inward portion that is disposed radially inward from the spiral portion,
- wherein the suture fastener, when in a resting state, has an unlocked conical helical configuration, in which the spiral portion is conically helical,
- wherein the suture fastener is configured, upon being axially plastically deformed, when one or more portions of the one or more sutures pass through respective portions of the suture fastener, to transition from the unlocked conical helical configuration to a locked planar spiral configuration, in which the spiral portion is planar spiral and the one or more sutures are fixedly coupled to the suture fastener, and
- wherein the radially-inward portion is neither helical nor spiral, both when the suture fastener is in the unlocked conical helical configuration and when the suture fastener is in the locked planar spiral configuration.

Inventive concept 25. The suture fastener according to Inventive concept 24, wherein the radially-inward portion is shaped so as to define a non-circular and non-spiral opening.

Inventive concept 26. The suture fastener according to Inventive concept 24, wherein a height of the suture fastener, when in the locked planar spiral configuration, is less than 5 mm.

Inventive concept 27. The suture fastener according to Inventive concept 24, wherein, when the suture fastener is in the locked planar spiral configuration, a height of the suture fastener is less than 25% of a greatest dimension of the suture fastener.

Inventive concept 28. The suture fastener according to Inventive concept 24, wherein an area of an upper surface of the radially-inward portion is between 5% and 15% of a total area of an upper surface of the suture fastener, including the radially-inward portion and the spiral portion.

Inventive concept 29. The suture fastener according to Inventive concept 24, wherein the suture fastener is shaped as a double helix in the unlocked conical helical configuration, and a double planar spiral in the locked planar spiral configuration.

Inventive concept 30. The suture fastener according to any one of Inventive concepts 24-29, further including sterile packaging, in which the suture fastener is removably disposed.

There is still further provided, in accordance with an Inventive concept 31 of the present invention, a surgical fastener system for fastening one or more sutures, the surgical fastener system including:
(a) a surgical fastener instrument, which includes:
- an outer delivery tube, which has a distal opening at a distal end of the outer delivery tube;
- an inner delivery shaft, which is disposed at least partially in the outer delivery tube; and
- a handle, which is coupled to a proximal portion of the outer delivery tube, and includes a user control element; and (b) a suture fastener, which is removably disposed in the outer delivery tube in an unlocked open configuration, in which the suture fastener is shaped so as to define a continuous loop that is shaped so as to define a central opening surrounded by the continuous loop, wherein the continuous loop includes first and second crimping portions, which are (i) joined to each other at first and second joining portions and (ii) disposed at different first and second axial locations, respectively, along a central longitudinal axis that passes through the opening defined by the continuous loop and is defined by both (A) the outer delivery tube and (B) the continuous loop, wherein the surgical fastener instrument is arranged such that activation of the user control element, when one or more portions of the one or more sutures pass through the central opening of the continuous loop, causes the inner delivery shaft of the surgical fastener to apply a lateral crimping force to at least one of the first and the second crimping portions that transitions the suture fastener from the unlocked open configuration to a locked closed configuration, in which a contact interface between the first and the second crimping portions creates friction that prevents sliding of the one or more sutures, thereby fixedly crimping the one or more sutures to the suture fastener, wherein the lateral crimping force is perpendicular to the central longitudinal axis.

Inventive concept 32. The surgical fastener system according to Inventive concept 31, wherein the suture fastener is configured to assume the unlocked open configuration when in a resting state, and wherein the surgical fastener instrument is arranged such that the activation of the user control element transitions the suture fastener from the unlocked open configuration to the locked closed configuration by plastically deforming the suture fastener.

There is additionally provided, in accordance with an Inventive concept 33 of the present invention, a surgical fastener system for fastening one or more sutures, the surgical fastener system including:
(a) a surgical fastener instrument, which includes:
- an outer delivery tube, which has a distal opening at a distal end of the outer delivery tube;
- an inner delivery shaft, which is disposed at least partially in the outer delivery tube; and
- a handle, which is coupled to a proximal portion of the outer delivery tube, and includes a user control element; and (b) a suture fastener, which is removably disposed in the outer delivery tube temporarily constrained by the surgical fastener instrument in an unlocked open configuration, in which the suture fastener is shaped so as to define a continuous loop that is shaped so as to define a central opening surrounded by the continuous loop, wherein the continuous loop includes first and second crimping portions, which are (i) joined to each other at first and second joining portions and (ii) disposed at different first and second axial locations, respectively, along a central longitudinal axis that passes through the opening defined by the continuous loop and is defined by both (A) the outer delivery tube and (B) the continuous loop, wherein the suture fastener is configured to assume, when in a resting state, a locked closed configuration, in which a contact interface between the first and the second crimping portions creates friction that prevents sliding of the one or more sutures, thereby fixedly crimping the one or more sutures to the suture fastener, and wherein the surgical fastener instrument is arranged such that activation of the user control element, when one or more portions of the one or more sutures pass through the central opening of the continuous loop, releases the suture fastener from being temporarily constrained by the surgical fastener instrument in the unlocked open configuration, such that the suture fastener automatically transitions to the closed locked configuration.

Inventive concept 34. The surgical fastener system according to any one of Inventive concepts 31 and 33, wherein, when the suture fastener is in the unlocked open configuration, the central longitudinal axis is parallel to an outer surface of the continuous loop facing away from the central longitudinal axis.

Inventive concept 35. The surgical fastener system according to any one of Inventive concepts 31 and 33, wherein, when the suture fastener is in the unlocked open configuration, the central longitudinal axis is parallel to an inner surface of the continuous loop facing toward the central longitudinal axis.

Inventive concept 36. The surgical fastener system according to any one of Inventive concepts 31 and 33, wherein, when the suture fastener is in the unlocked open configuration, each of the first and the second crimping portions defines a portion of a cylinder.

Inventive concept 37. The surgical fastener system according to Inventive concept 36, wherein, when the suture fastener is in the unlocked open configuration, each of the first and the second crimping portions is generally half-cylindrical.

Inventive concept 38. The surgical fastener system according to any one of Inventive concepts 31 and 33, wherein, when the suture fastener is in the unlocked open configuration, the first and the second different axial locations at which the first and the second crimping portions are respectively disposed do not axially overlap or axially overlap by less than 1 mm.

Inventive concept 39. The surgical fastener system according to any one of Inventive concepts 31 and 33, wherein, when the suture fastener is in the unlocked open configuration, an average distance of the first crimping portion from the central longitudinal axis equals between 75% and 125% of an average distance of the second crimping portion from the central longitudinal axis.

Inventive concept 40. The surgical fastener system according to any one of Inventive concepts 31 and 33, wherein, when the suture fastener is in the locked closed configuration, the contact interface includes a straight portion.

Inventive concept 41. The surgical fastener system according to any one of Inventive concepts 31 and 33, wherein a height of the suture fastener, measured along the central longitudinal axis, both when in the unlocked open configuration and the locked closed configuration, is less than 20 mm.

Inventive concept 42. The surgical fastener system according to Inventive concept 41, wherein the height of the suture fastener, measured along the central longitudinal axis, both when in the unlocked open configuration and the locked closed configuration, is less than 7 mm.

Inventive concept 43. The surgical fastener system according to any one of Inventive concepts 31 and 33, wherein a height of the suture fastener when in the unlocked open configuration equals a height of the suture fastener when in the locked closed configuration.

Inventive concept 44. The surgical fastener system according to any one of Inventive concepts 31 and 33, wherein the surgical fastener instrument further includes one or more blades, which are configured to cut the one or more sutures.

Inventive concept 45. The surgical fastener system according to any one of Inventive concepts 31-44, wherein the surgical fastener instrument is arranged such that the activation of the user control element transitions the suture fastener from the unlocked open configuration to the locked closed configuration while the suture fastener is disposed entirely within the outer delivery tube.

Inventive concept 46. The surgical fastener system according to any one of Inventive concepts 31-44, wherein the outer delivery tube is shaped so as to define one or more lateral openings that extend to the distal end, and facilitate insertion of the one or more portions of the one or more sutures into the outer delivery tube and through the central opening of the continuous loop of the suture fastener.

Inventive concept 47. The surgical fastener system according to any one of Inventive concepts 31-44, wherein the surgical fastener system includes a plurality of suture fasteners, which are removably disposed in the outer delivery tube, each in an unlocked open configuration.

Inventive concept 48. The surgical fastener system according to any one of Inventive concepts 31-44, further including sterile packaging, in which the suture fastener is removably disposed.

There is yet additionally provided, in accordance with an Inventive concept 49 of the present invention, a method for fastening one or more sutures, the method including:

passing one or more portions of one or more sutures through respective portions of a suture fastener while the suture fastener is in an unlocked conical helical configuration; and transitioning the suture fastener from the unlocked conical helical configuration to a locked planar spiral configuration, in which the one or more sutures are fixedly coupled to the suture fastener.

Inventive concept 50. The method according to Inventive concept 49, wherein the suture fastener is configured to assume the unlocked conical helical configuration when in a resting state, and wherein transitioning the suture fastener from the unlocked conical helical configuration to the locked planar spiral configuration includes axially plastically deforming the suture fastener.

Inventive concept 51. The method according to Inventive concept 49, wherein passing the one or more portions of the one or more sutures through respective portions of the suture fastener includes rotating the suture fastener.

Inventive concept 52. The method according to Inventive concept 51, wherein passing the one or more portions of the one or more sutures through respective portions of the suture fastener includes entangling the one or more portions of the one or more sutures with the respective portions of the suture fastener.

Inventive concept 53. The method according to Inventive concept 49, wherein a height of the suture fastener, when in the locked planar spiral configuration, is less than 5 mm.

Inventive concept 54. The method according to Inventive concept 49, wherein, when the suture fastener is in the locked planar spiral configuration, a height of the suture fastener is less than 25% of a greatest dimension of the suture fastener.

Inventive concept 55. The method according to Inventive concept 49, wherein the suture fastener is shaped so as to define a spiral portion, which is (a) conically helical when the suture fastener is in the unlocked conical helical configuration and (b) planar spiral when the suture fastener is in the planar spiral configuration, and wherein the suture fastener is shaped so as to define a radially-inward portion that, both when the suture fastener is in the unlocked conical helical configuration and when the suture fastener is in the locked planar spiral configuration, (a) is neither helical nor spiral, and (b) is disposed radially inward from the spiral portion.

Inventive concept 56. The method according to Inventive concept 55, wherein the radially-inward portion is shaped so as to define a non-circular and non-spiral opening.

Inventive concept 57. The method according to Inventive concept 55, wherein an area of an upper surface of the radially-inward portion is between 5% and 15% of a total area of an upper surface of the suture fastener, including the radially-inward portion and the spiral portion.

There is also provided, in accordance with an Inventive concept 58 of the present invention, a method for fastening one or more sutures, the method including:
passing one or more portions of one or more sutures through respective portions of a suture fastener while the suture fastener is in an unlocked open configuration, in which the suture fastener is shaped so as to define a continuous loop that is shaped so as to define a central opening surrounded by the continuous loop, wherein the continuous loop includes first and second crimping portions, which are (i) joined to each other at first and second joining portions and (ii) disposed at different first and second axial locations, respectively, along a central longitudinal axis that passes through the opening defined by the continuous loop and is defined by the continuous loop; and transitioning the suture fastener from the unlocked open configuration to a locked closed configuration, in which a contact interface between the first and the second crimping portions creates friction that prevents sliding of the one or more sutures, thereby fixedly crimping the one or more sutures to the suture fastener.

Inventive concept 59. The method according to Inventive concept 58, wherein, when the suture fastener is in the unlocked open configuration, the central longitudinal axis is parallel to an outer surface of the continuous loop facing away from the central longitudinal axis.

Inventive concept 60. The method according to Inventive concept 58, wherein, when the suture fastener is in the unlocked open configuration, the central longitudinal axis is parallel to an inner surface of the continuous loop facing toward the central longitudinal axis.

Inventive concept 61. The method according to Inventive concept 58,
wherein the suture fastener is configured to assume the unlocked open configuration when in a resting state, and transitioning the suture fastener from the unlocked open configuration to the locked closed configuration includes applying a lateral crimping force to at least one of the first and the second crimping portions that plastically deforms the suture fastener, wherein the lateral crimping force is perpendicular to the central longitudinal axis.

Inventive concept 62. The method according to Inventive concept 58,
wherein the suture fastener is configured to assume the locked closed configuration when in a resting state, and wherein passing the one or more portions of the one or more sutures includes passing the one or more portions of the one or more sutures through the respective portions of the suture fastener while the suture fastener is temporarily constrained in the unlocked open configuration, and wherein transitioning the suture fastener from the unlocked open configuration to the locked closed configuration includes releasing the suture fastener from being temporarily constrained in the unlocked open configuration, such that the suture fastener automatically transitions to the closed locked configuration.

Inventive concept 63. The method according to Inventive concept 58, wherein, when the suture fastener is in the unlocked open configuration, each of the first and the second crimping portions defines a portion of a cylinder.

Inventive concept 64. The method according to Inventive concept 63, wherein, when the suture fastener is in the unlocked open configuration, each of the first and the second crimping portions is generally half-cylindrical.

Inventive concept 65. The method according to Inventive concept 58, wherein, when the suture fastener is in the unlocked open configuration, the first and the second different axial locations at which the first and the second crimping portions are respectively disposed do not axially overlap or axially overlap by less than 1 mm.

Inventive concept 66. The method according to Inventive concept 58, wherein, when the suture fastener is in the unlocked open configuration, an average distance of the first crimping portion from the central longitudinal axis equals between 75% and 125% of an average distance of the second crimping portion from the central longitudinal axis.

Inventive concept 67. The method according to Inventive concept 58, wherein, when the suture fastener is in the locked closed configuration, the contact interface includes a straight portion.

Inventive concept 68. The method according to Inventive concept 58, wherein a height of the suture fastener, measured along the central longitudinal axis, both when in the unlocked open configuration and the locked closed configuration, is less than 20 mm.

Inventive concept 69. The method according to Inventive concept 68, wherein the height of the suture fastener, measured along the central longitudinal axis, both when in the unlocked open configuration and the locked closed configuration, is less than 7 mm.

Inventive concept 70. The method according to Inventive concept 58, wherein a height of the suture fastener when in the unlocked open configuration equals a height of the suture fastener when in the locked closed configuration.

The present invention will be more fully understood from the following detailed description of embodiments thereof, taken together with the drawings, in which:

BRIEF DESCRIPTION OF THE DRAWINGS

FIGS. 4 and 5A-B are schematic illustrations of the use of the surgical fastener system of FIG. 1 to fasten an annuloplasty ring to the mitral valve during a surgical procedure, in accordance with an application of the present invention;

FIGS. 9A-F are schematic illustrations of the use of a surgical fastener instrument of the surgical fastener system of FIG. 1 for crimping a single suture fastener of the surgical fastener system of FIG. 1, in accordance with an application of the present invention;

FIGS. 10A-F are schematic illustrations of another use of a surgical fastener instrument of the surgical fastener system of FIG. 1 for crimping a single suture fastener of the surgical fastener system of FIG. 1, in accordance with an application of the present invention;

DETAILED DESCRIPTION OF APPLICATIONS

Figure 1:
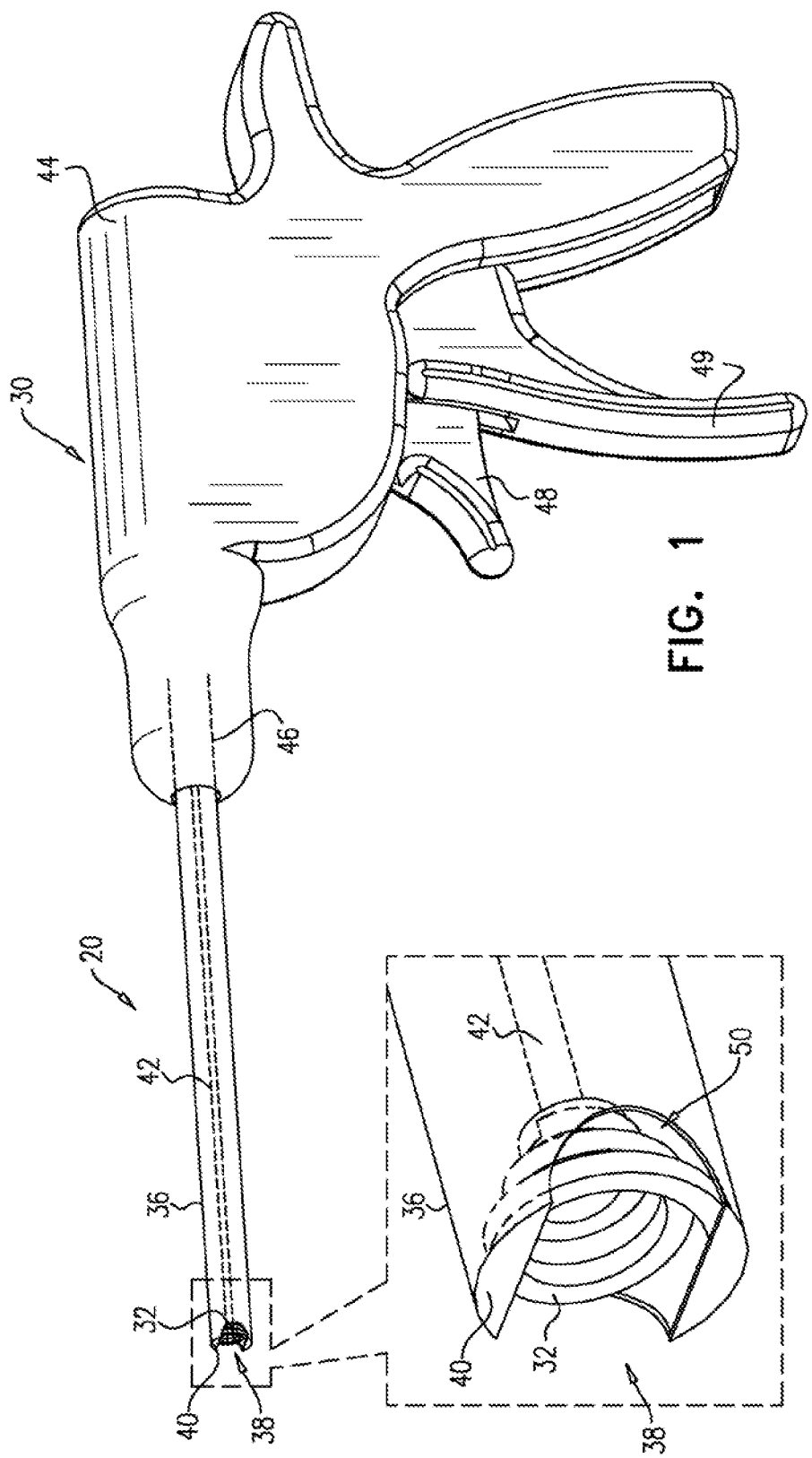
FIG. 1 is a schematic illustration of a surgical fastener system for fastening one or more sutures, in accordance with an application of the present invention.

FIG. 1 is a schematic illustration of a surgical fastener system 20 for fastening one or more sutures 22, in accordance with an application of the present invention. The one or more sutures 22 shown in FIGS. 4, 5A-B, 7B-D, 8A-C, 9A-F, 10A-F, and 11A-F are typically not elements of surgical fastener system 20.

Surgical fastener system 20 comprises a surgical fastener instrument 30 and a suture fastener 32, typically a plurality of suture fasteners 32. Surgical fastener instrument 30 comprises:

an outer delivery tube 36, which has a distal opening 38 at a distal end 40 of outer delivery tube 36;
an inner delivery shaft 42, which is disposed at least partially in outer delivery tube 36; and
a handle 44, which is coupled to a proximal portion 46 of outer delivery tube 36, and comprises a user control element 48, e.g., a knob, trigger, or button, arranged to rotate inner delivery shaft 42 with respect to outer delivery tube 36.

Typically, user control element 48 is operated by the palm and fingers of the operator using wrist and finger movement, using little force. For some applications, handle 44 comprises a plurality of user control elements 48, for controlling the different functions of surgical fastener instrument 30 during the several steps of its use, as described hereinabove with reference to FIGS. 9A-F. For example, user control element 48 may be a first user control element 48, and handle 44 may comprise a second user control element 49, which is arranged to cause distal advancement of inner delivery shaft 42 (typically with respect to outer delivery tube 36).

For some applications, user control element 48 is arranged to both rotate inner delivery shaft 42 with respect to outer delivery tube 36 and to cause the distal advancement of inner delivery shaft 42 (typically with respect to outer delivery tube 36). Typically, user control element 48 is arranged to begin causing the distal advancement of inner delivery shaft 42 after beginning rotating of inner delivery shaft 42. Optionally, user control element 48 is arranged to begin causing the distal advancement of inner delivery shaft 42 after completing rotating of inner delivery shaft 42. Alternatively or additionally, user control element 48 may be arranged to cause the distal advancement of inner delivery shaft 42, and thereafter cause one or more blades of surgical fastener instrument 30 to cut the one or more sutures 22, such as described hereinbelow with reference to FIG. 14, mutatis mutandis.

Figure 2A:
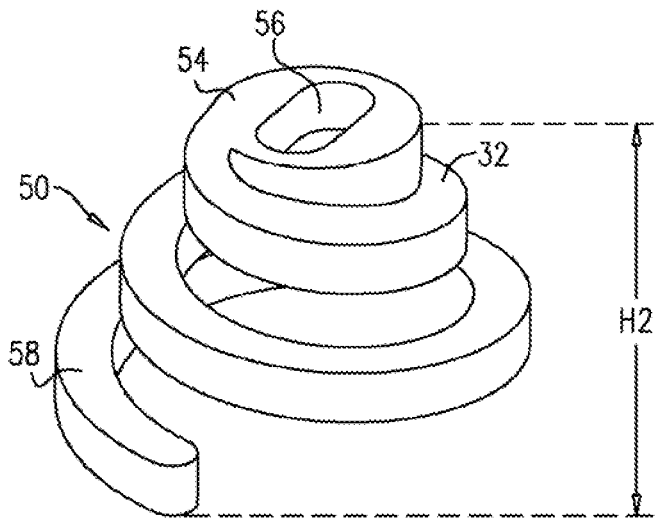
FIGS. 2A-C are schematic illustrations of a suture fastener of the surgical fastener system of FIG. 1, in accordance with an application of the present invention.

Suture fastener 32 is removably disposed in outer delivery tube 36 in an unlocked conical helical configuration 50 (which may be considered an uncrimped or open configuration), such as, for example, shown in FIG. 2A. Surgical fastener instrument 30 is arranged such that distal advancement of inner delivery shaft 42, when one or more portions of the one or more sutures 22 pass through respective portions of suture fastener 32, transitions suture fastener 32 from unlocked conical helical configuration 50 to a locked planar spiral configuration 52, such as, for example, shown in FIGS. 2B-C, by a distal portion of inner delivery shaft 42 pushing on a proximal portion of suture fastener 32. In locked planar spiral configuration 52 (which may be considered a crimped configuration), the one or more sutures 22 are fixedly coupled to suture fastener 32 (as shown in FIGS. 9D-F and 10D-F). This transitioning may be considered crimping suture fastener 32 to the one or more sutures 22. (It is noted that surgical fastener instrument 30 is arranged such that the distal advancement of inner delivery shaft 42 transitions suture fastener 32 from unlocked conical helical configuration 50 to locked planar spiral configuration 52 even if no sutures 22 pass through suture fastener 32, although surgical fastener instrument 30 is not intended to be used without at least one suture.) As used in the present application, including in the claims, when suture fastener 32 is in the unlocked conical helical configuration 50, suture fastener 32 is not necessarily entirely helical, and when suture fastener 32 is in the locked planar spiral configuration 52, suture fastener 32 is not necessarily entirely planar spiral; for example, suture fastener 32 may be shaped so as define one or more non-helical portions, such as the radially-inward center portion described hereinbelow.

For some applications, a plurality of suture fasteners 32 are removably disposed in outer delivery tube 36 in unlocked conical helical configurations 50, and surgical fastener instrument 30 is configured to deploy the suture fasteners one at a time (configuration not shown).

Figure 2B:
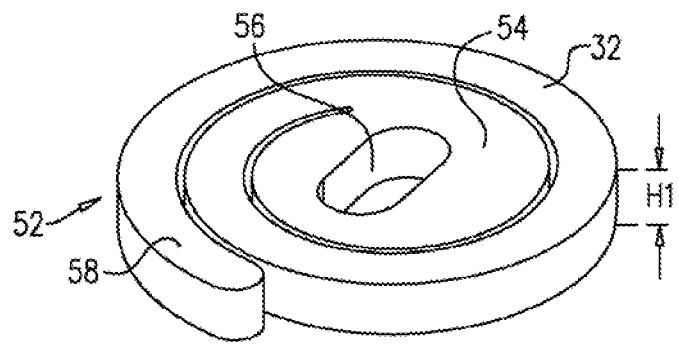
Figure 2C:
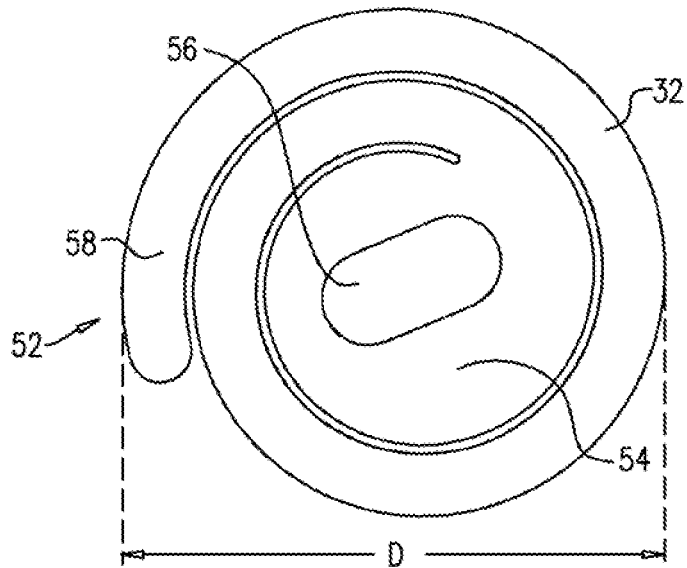

Reference is now made to FIGS. 2A-C, which are schematic illustrations of suture fastener 32, in accordance with an application of the present invention. In FIG. 2A, suture fastener 32 is shown in unlocked conical helical configuration 50. In FIGS. 2B and 2C, suture fastener 32 is shown in locked planar spiral configuration 52.

For some applications:
- a height H1 of suture fastener 32 (labeled in FIG. 2B), when in locked planar spiral configuration 52, is at least 0.02 and/or less than 5 mm, such as less than 4 mm, e.g., less than 3 mm,
- a height H2 of suture fastener 32 (labeled in FIG. 1B), when in unlocked conical helical configuration 50, is at least 1 and/or less than 20 mm,
- height H1 equals between 2% and 25% of H2, such as between 2% and 20%, e.g., 2% and 15% of H2,
- when suture fastener 32 is in locked planar spiral configuration 52, height H1 of suture fastener 32 is at least 5% and/or less than 25% (e.g., less than 20%, such as less than 15%) of a greatest dimension D of suture fastener 32, and/or
- when suture fastener 32 is in locked planar spiral configuration 52, greatest dimension D of suture fastener 32 (labeled in FIG. 2C) is at least 2 and/or less than 20 mm.

The above-mentioned relatively low height H1, i.e., low profile (compared to known surgical fasteners) results in a relatively low offset of suture fastener 32 from the prosthesis (compared to known surgical fasteners), which may reduce the likelihood of damaging surround tissue or prosthesis components.

For some applications, the conical helices and planar spirals of suture fastener 32 have between 1 and 7 turns, such as two, three, or four turns.

For some applications, suture fastener 32 is configured to assume unlocked conical helical configuration 50 when in a resting state. For these applications, surgical fastener instrument 30 is arranged such that the distal advancement of inner delivery shaft 42 transitions suture fastener 32 from unlocked conical helical configuration 50 to locked planar spiral configuration 52 by axially plastically deforming suture fastener 32. For these applications, suture fastener 32 typically comprises a metal such as titanium, tantalum, gold, silver, platinum-iridium, cobalt-chromium, or stainless steel.

Alternatively, for some applications, suture fastener 32 is configured to assume locked planar spiral configuration 52 when in a resting state, and surgical fastener instrument 30 is arranged to temporarily constrain suture fastener 32 in unlocked conical helical configuration 50. For these applications, suture fastener 32 typically comprises a metal having a shape memory, such as a superelastic metal, e.g., Nitinol.

For some applications, suture fastener 32 is shaped so as to define a radially-inward portion 54 that is neither helical nor spiral, both when suture fastener 32 is in unlocked conical helical configuration 50 and when suture fastener 32 is in locked planar spiral configuration 52. Radially-inward portion 54 is typically shaped so as to define a non-circular and non-spiral opening 56, as shown in the figures. This shape of opening 56 may aid in engagement of suture fastener 32 by the distal end of inner delivery shaft 42, which may be shaped, for example, like a conventional flat screwdriver head. In these applications, suture fastener 32 is shaped so as to define a spiral portion 58, which is (a) conically helical when suture fastener 32 is in unlocked conical helical configuration 50 and (b) planar spiral when suture fastener is in planar spiral configuration 52. Radially-inward portion 54 is disposed radially inward from spiral portion 58, both when suture fastener 32 is in unlocked conical helical configuration 50 and when suture fastener 32 is in locked planar spiral configuration 52.

For some applications, an area of an upper surface of radially-inward portion 54 is at least 5 mm2, no more than 15 mm2, and/or between 5 and 15 mm2. Alternatively or additionally, for some applications, a total area of an upper surface of suture fastener 32, including radially-inward portion 54 and spiral portion 58, is at least 25 mm2, no more than 75 mm2, and/or between 25 and 75 mm2. Further alternatively or additionally, for some applications, an area of an upper surface of radially-inward portion 54 is at least 5% (e.g., at least 10%), no more than 25% (e.g., no more than 15%, and/or between 5% (e.g., 10%) and 25% (e.g., 15%) of a total area of an upper surface of suture fastener 32, including radially-inward portion 54 and spiral portion 58. (In configurations in which radially-inward portion 54 is shaped so as to define opening 56, the above-mentioned areas exclude the area of opening 56.)

Figure 3A:
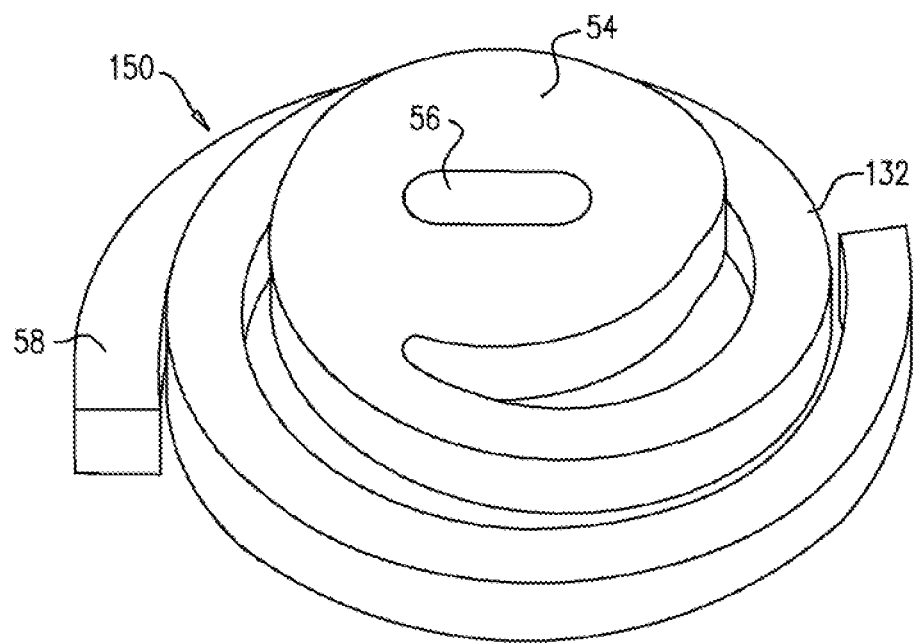
FIGS. 3A-B are schematic illustrations of another suture fastener in an unlocked conical helical configuration and a locked planar spiral configuration, respectively, in accordance with an application of the present invention.
Figure 3B:
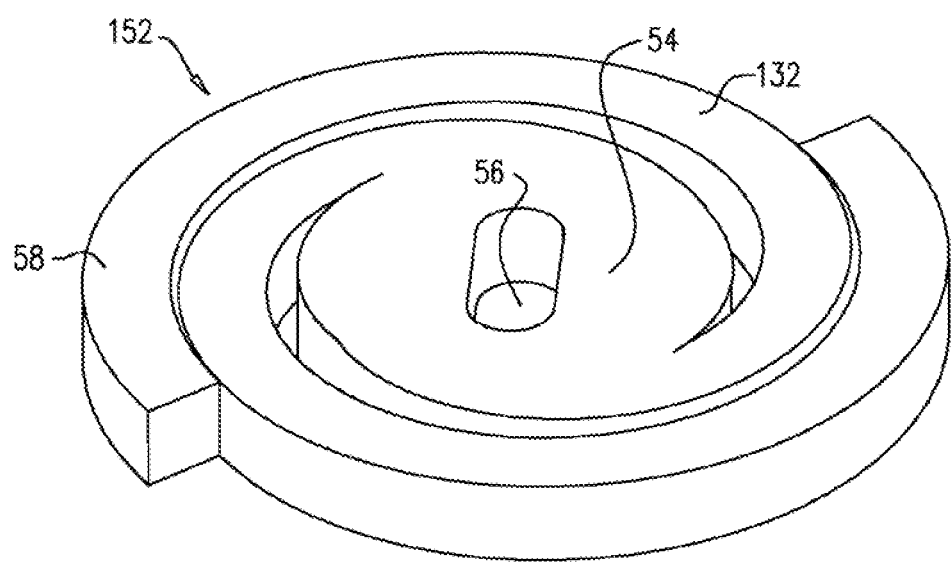

Reference is now made to FIGS. 3A-B, which are schematic illustrations of a suture fastener 132 in an unlocked conical helical configuration 150 and a locked planar spiral configuration 152, respectively, in accordance with an application of the present invention. Other than as described below, suture fastener 132 is similar to suture fastener 32, described hereinabove, and may implement any of the features thereof, and surgical fastener instrument 30 may be used to deploy suture fastener 132 in the same manner as suture fastener 32.

Suture fastener 132 is shaped as a double conical helix in unlocked conical helical configuration 150, and a double planar spiral in locked planar spiral configuration 152. This double helical configuration allows the one or more suture 22 to remain entangled within the spiral space between the two helical arms of suture fastener 132 when in unlocked conical helical configuration 150. The crimping of the helical arms in locked planar spiral configuration 152 strengthens the tightening of the one or more sutures 22 because of the friction created by the crimped structure, leaving the one or more sutures 22 in place. In addition, this double helical configuration may allow the securement of more sutures 22, and access of the sutures 22 to suture fastener 132 from more than one specific direction, increasing the entanglement of the sutures 22 within at least one spiral during rotating of inner delivery shaft 42, as described above. Suture fastener 132 may be deployed using the techniques described in the same manner as suture fastener 32, mutatis mutandis.

Figure 3C:
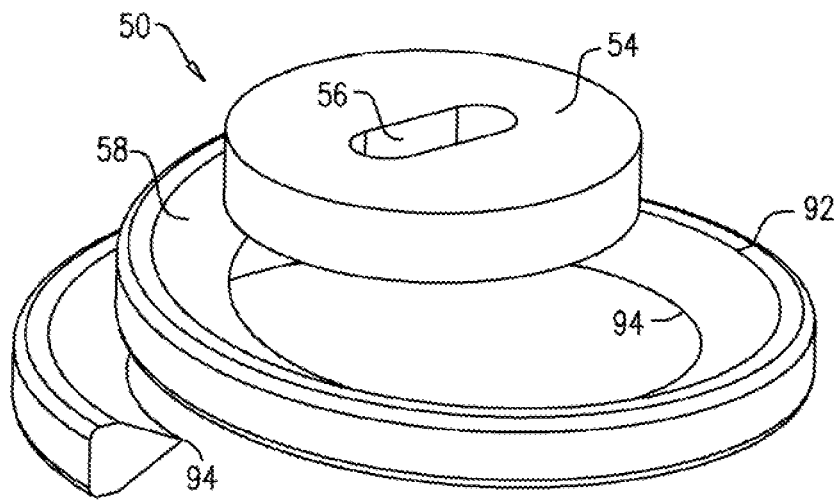
FIGS. 3C-D are schematic illustrations of another suture fastener, in accordance with an application of the present invention.
Figure 3D:
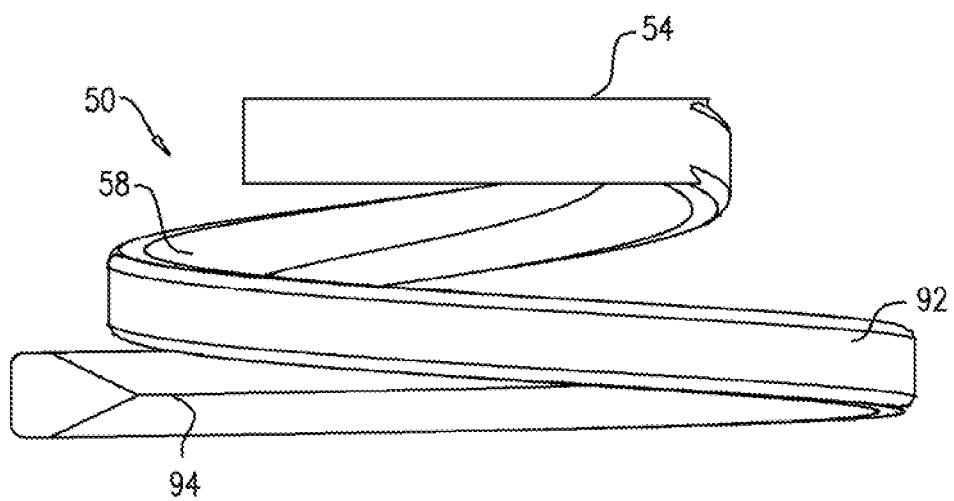

Reference is now made to FIGS. 3C-D, which are schematic illustrations of a suture fastener 92, in accordance with an application of the present invention. Other than as described below, suture fastener 92 is similar to suture fastener 32, and may implement any of the features thereof. Suture fastener 92 is shown in FIGS. 3C-D in unlocked conical helical configuration 50.

Suture fastener 92 is shaped so as to define one or more blades 94 (e.g., a single blade 94, as shown), which are configured to cut the one or more sutures 22 upon rotation of suture fastener 92, after crimping of the suture fastener. Typically, suture fastener 92 first engages with the one or more sutures 22 by rotation, and then the suture fastener is crimped using handle 44 of surgical fastener instrument 30; subsequently, suture fastener 92 rotates a bit further to fully cut the one or more sutures 22. For example, the one or more blades 94 (e.g., a single blade 94, as shown) may be defined by a surface of spiral portion 58 that faces radially inward.

Figure 3E:
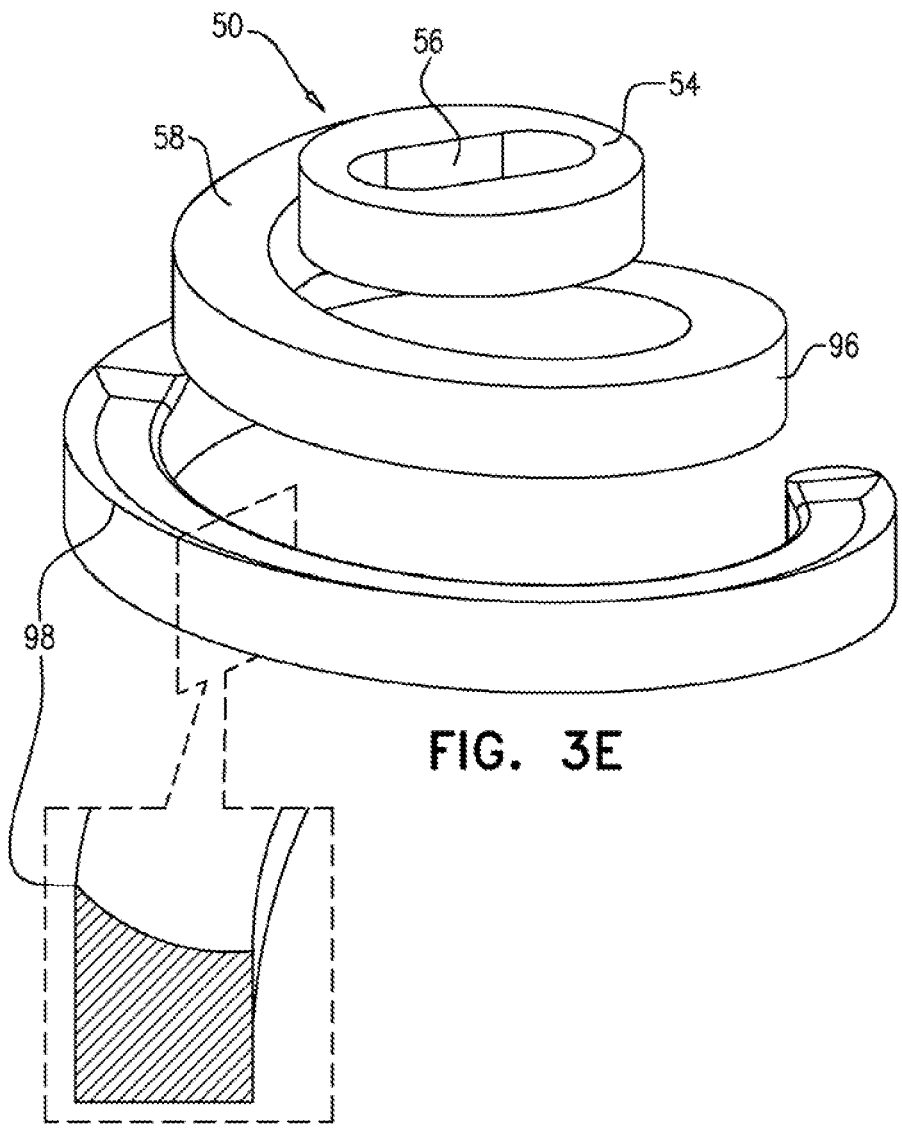
FIG. 3E is a schematic illustration of yet another suture fastener, in accordance with an application of the present invention.

Reference is now made to FIG. 3E, which is a schematic illustration of a suture fastener 96, in accordance with an application of the present invention. Other than as described below, suture fastener 96 is similar to suture fastener 32, and may implement any of the features thereof. Suture fastener 96 is shown in FIG. 3E in unlocked conical helical configuration 50.

Suture fastener 96 is shaped so as to define one or more blades 98 (e.g., a single blade 98, as shown), which are configured to cut the one or more sutures 22 upon directing of the one or more suture 22 against the one or more blades 98, after crimping of the suture fastener. For example, the one or more blades 98 (e.g., a single blade 98, as shown) may be defined by:
- a surface of spiral portion 58 that faces radially upward, i.e., in the direction of radially-inward portion 54 when suture fastener 32 is in unlocked conical helical configuration 50,
- a radially-outward edge of spiral portion 58, and/or
- a portion or all of an outermost turn of spiral portion 58.

Typically, suture fastener 96 first engages with the one or more sutures 22 by rotation, and then the suture fastener is crimped using handle 44 of surgical fastener instrument 30; subsequently, the one or more sutures are tensioned and angled against the one or more blades 98 of the fastener 96 to fully cut the one or more sutures 22, while leaving portions of the one or more sutures crimped to the suture fastener.

Figure 4:
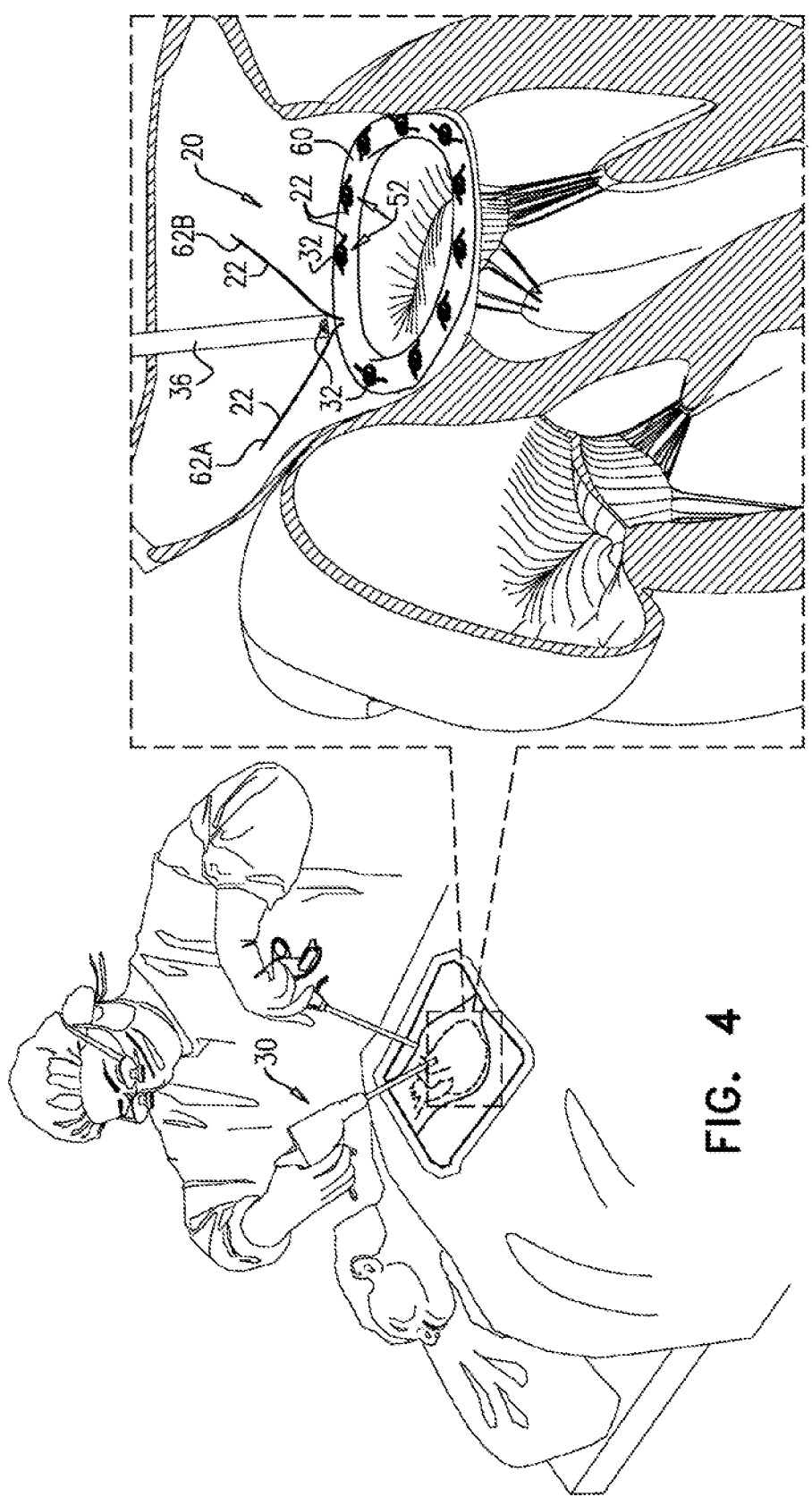
Figure 6:
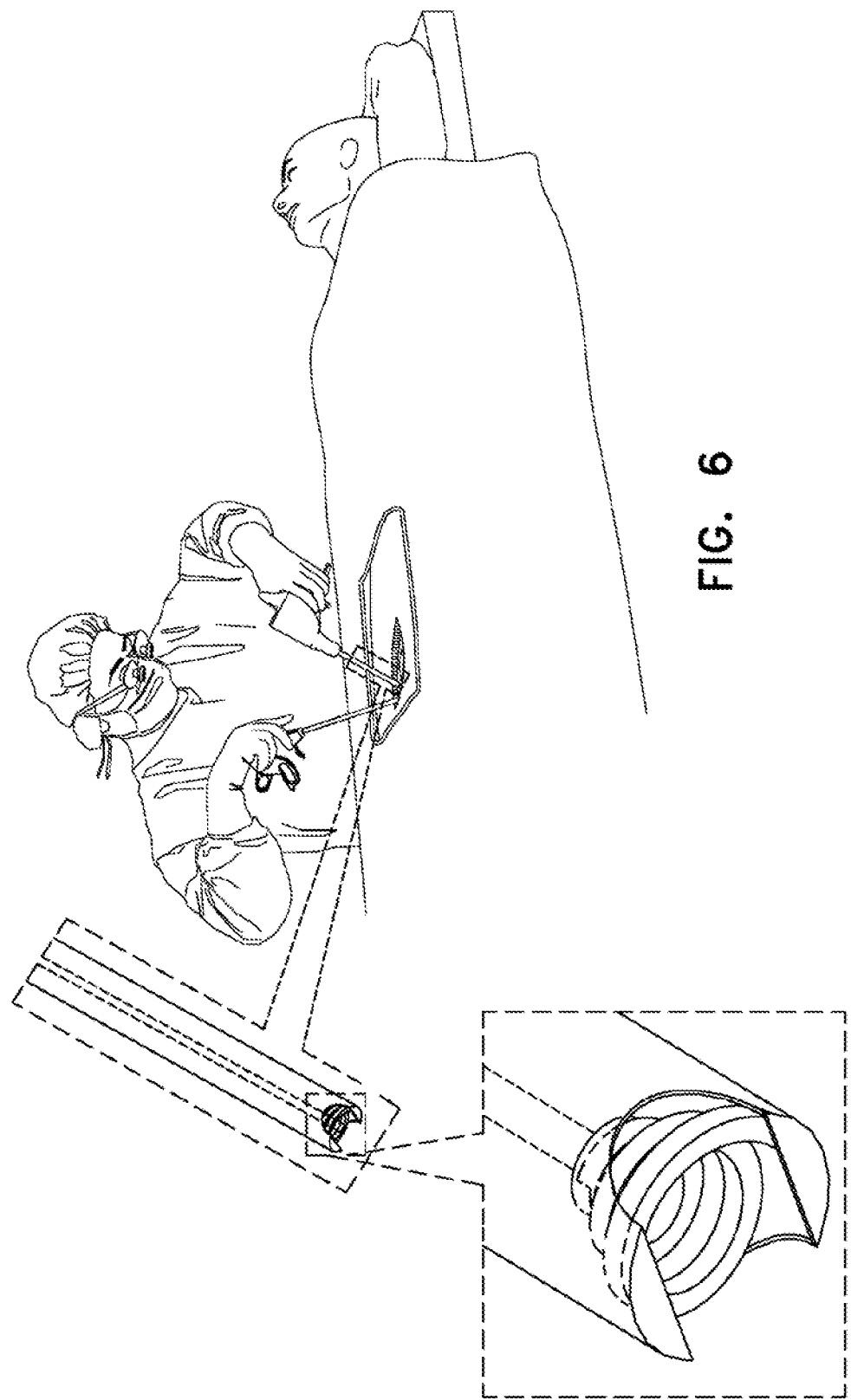
FIGS. 6 and 7A-D are schematic illustrations of the use of the surgical fastener system of FIG. 1 to fasten a suture used to perform anastomosis during another surgical procedure, in accordance with an application of the present invention.

Reference is now made to FIGS. 4 and 5A-B, which are schematic illustrations of the use of surgical fastener system 20 to fasten an annuloplasty ring 60 to the mitral valve during a surgical procedure, in accordance with an application of the present invention. By way of example and not limitation, FIGS. 4 and 5A-B show surgical fastener system 20 being used to fasten annuloplasty ring 60 to the mitral valve, as is known in the mitral valve repair art. In FIGS. 4 and 5B, a plurality of suture fasteners 32 are shown after locking (crimping) in their locked planar spiral configurations 52, and the last of suture fasteners 32 is shown during crimping using surgical fastener instrument 30. Although the procedure is shown using suture fasteners 32, the other suture fasteners described herein may alternatively be used.

Reference is now made to FIGS. 6 and 7A-D, which are schematic illustrations of the use of surgical fastener system 20 to fasten a suture 22 used to perform anastomosis during another surgical procedure, in accordance with an application of the present invention. By way of example and not limitation, FIGS. 6 and 7A-D show surgical fastener system 20 being used to fasten a suture 22 used to perform anastomosis, as is known in the anastomosis surgical art. Although the procedure is shown using suture fastener 32, the other suture fasteners described herein may alternatively be used.

Figure 7A:
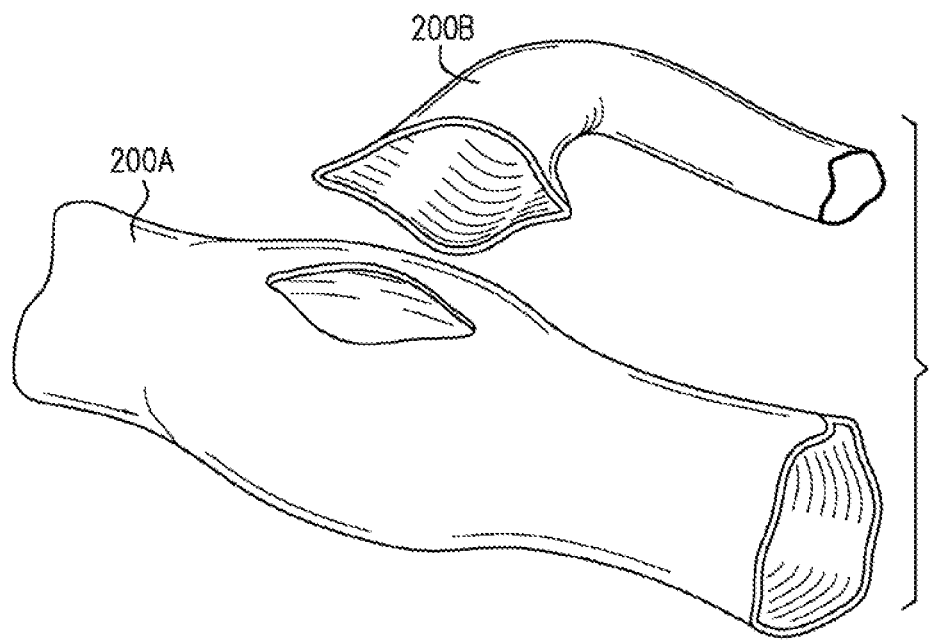

FIG. 7A shows two blood vessels 200A and 200B to be anastomosed. For example, the two blood vessels may be two arteries (arterio-arterial anastomosis), two veins (venovenous anastomosis), an artery and a vein (arterio-venous anastomosis), or a blood vessel and an artificial blood-carrying vessel, as is known in the anastomosis surgical art.

Figure 7B:
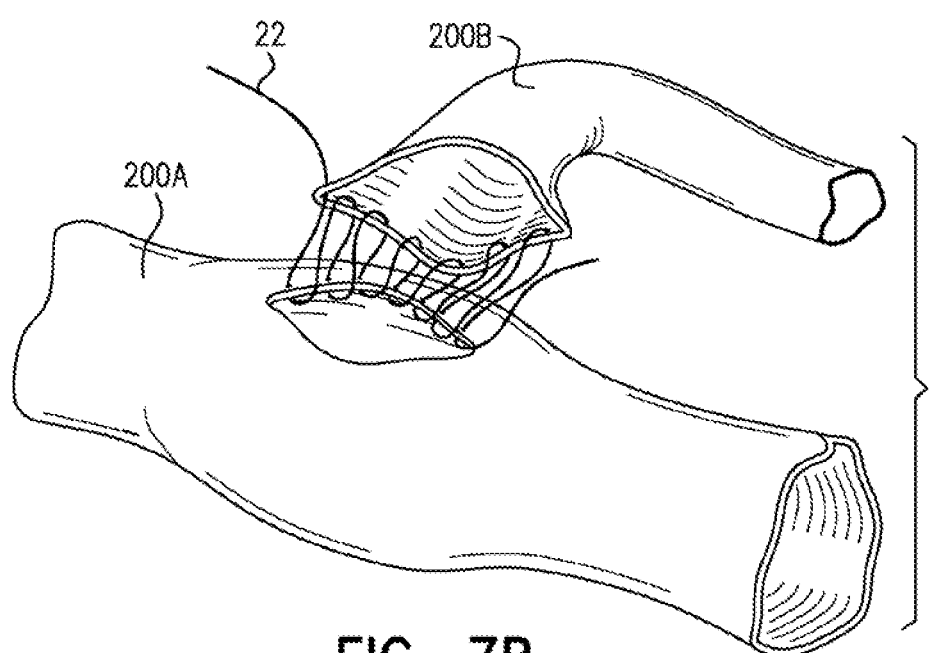

As shown in FIG. 7B, the two blood vessels 200A and 200B are sutured together using a suture 22, as is known in the anastomosis surgical art.

Figures 7C, 7D:
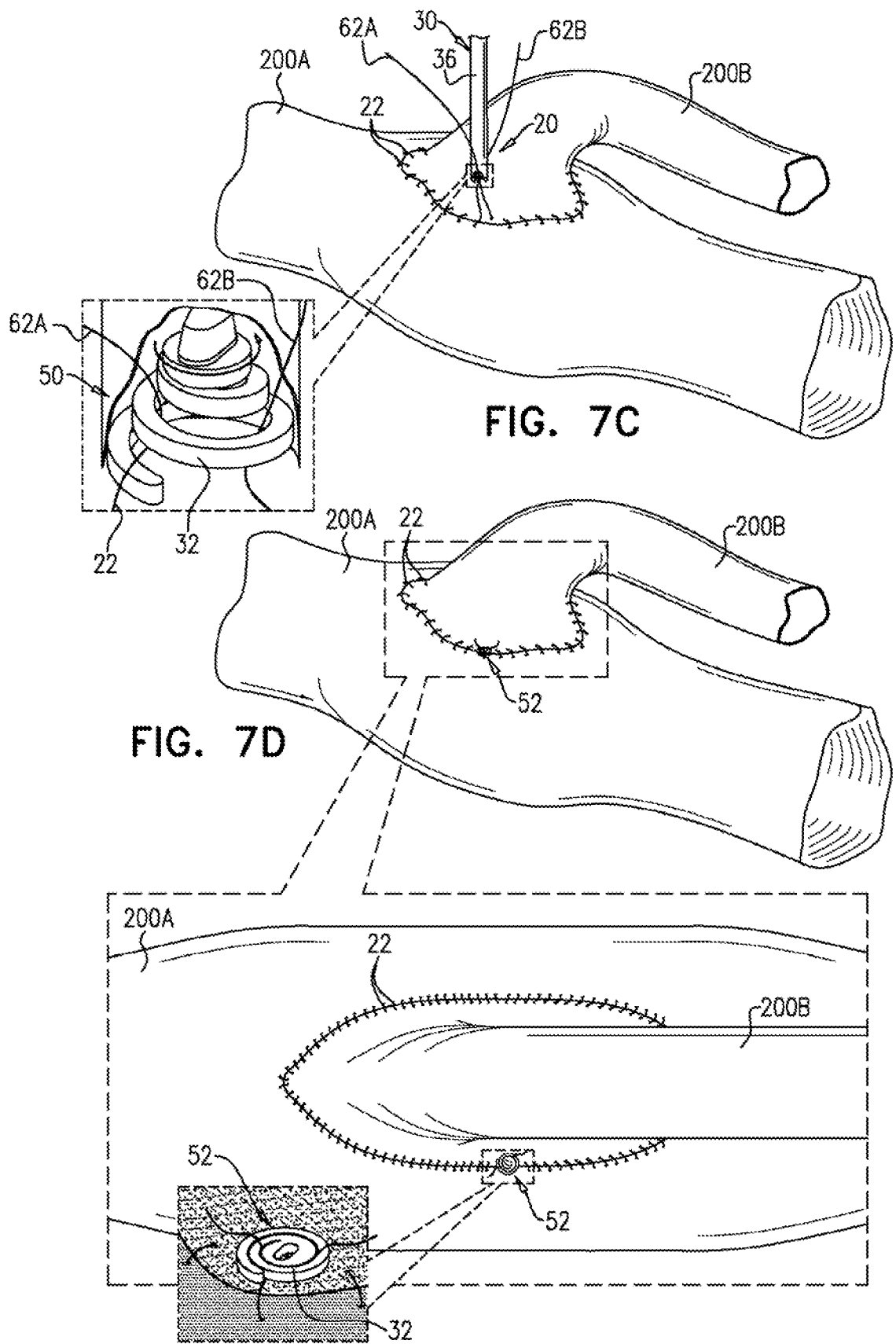

As shown in FIG. 7C, surgical fastener system 20 is used to fasten two loose portions 62A and 62B of suture 22 together.

As shown in FIG. 7D, surgical fastener instrument 30 used to entangle the suture two portions 62A and 62B with suture fastener 32 and transition suture fastener 32 to locked planar spiral configuration 52, and, optionally, to cut excess suture portions 62A and 62B, stabilizing suture 22 on the anastomosis. Alternatively, a separate, conventional surgical tool is used to cut the excess suture portions, as is known in the surgical art. If necessary, more than one suture fastener 32 may be used to fasten the suture ends together, if the surgeon believes it to be necessary.

Figure 8A:
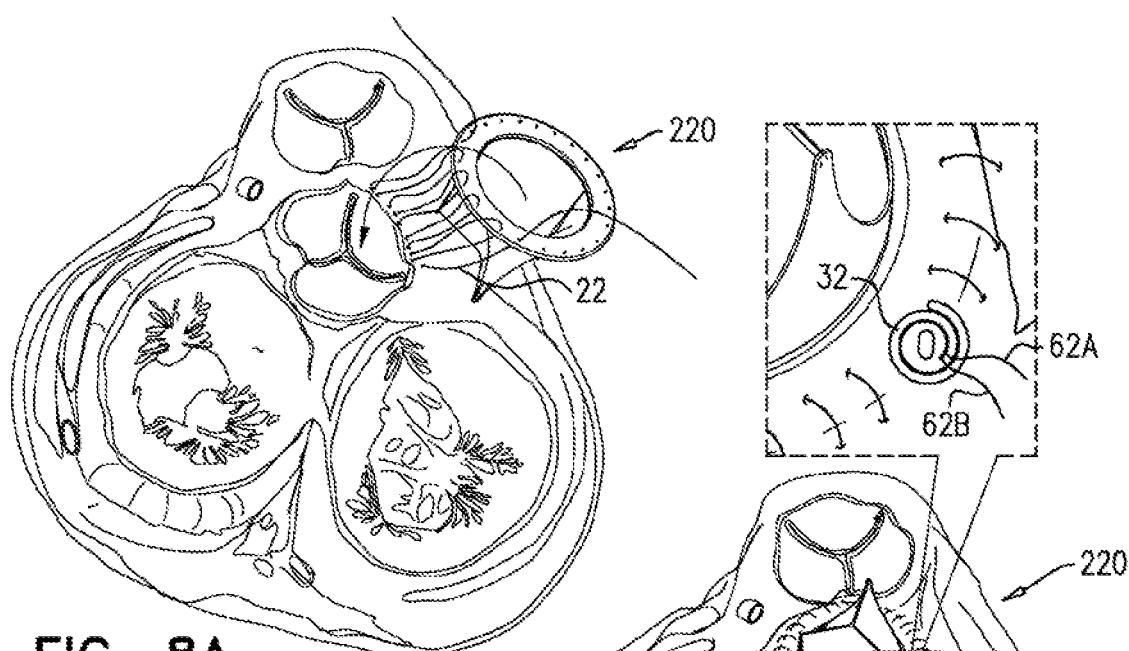
FIGS. 8A-C are schematic illustrations of the use of the surgical fastener system of FIG. 1 to fasten a prosthetic aortic valve during an aortic valve replacement (AVR) surgical procedure, in accordance with an application of the present invention.
Figure 8B:
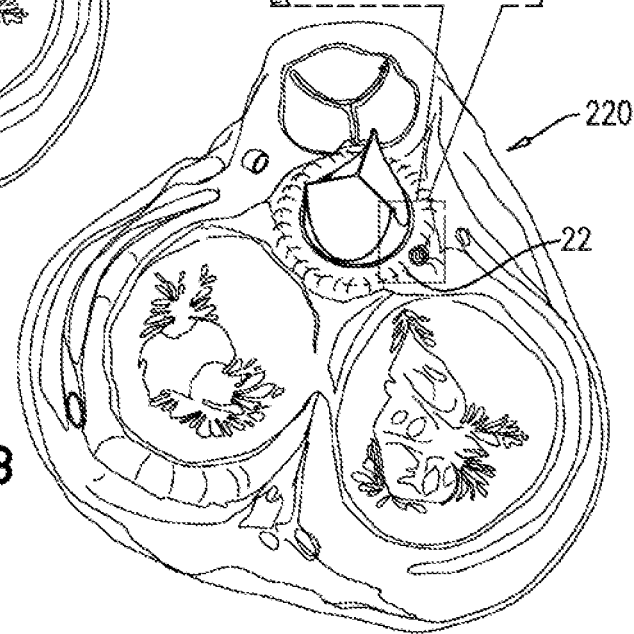
Figure 8C:
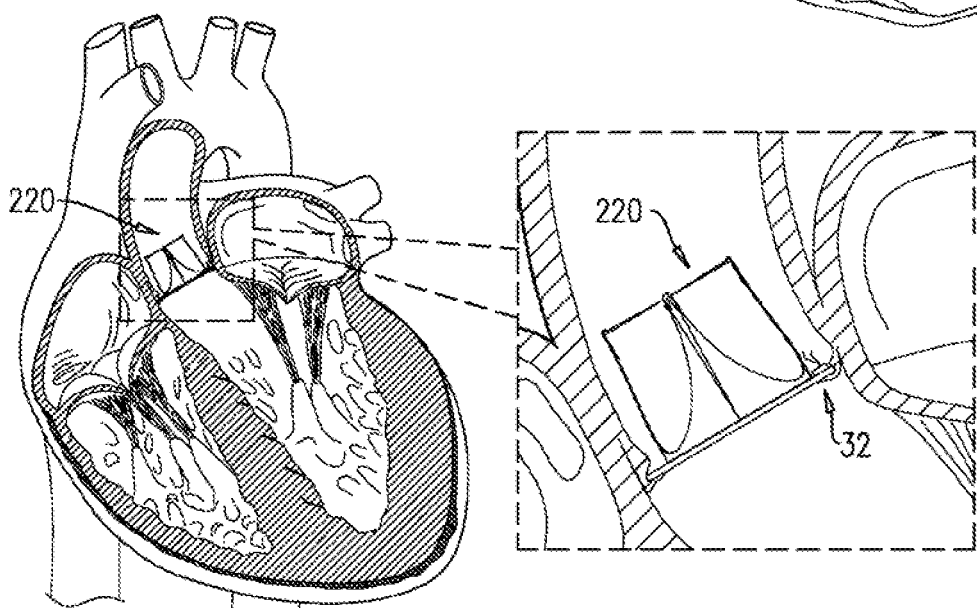

Reference is now made to FIGS. 8A-C, which are schematic illustrations of the use of surgical fastener system 20 to fasten a prosthetic aortic valve 220 during an aortic valve replacement (AVR) surgical procedure, in accordance with an application of the present invention. The above-mentioned relatively low height H1, i.e., low profile (compared to known surgical fasteners) results in a relatively low offset of suture fastener 32 from the prosthesis (compared to known surgical fasteners), which may reduce the likelihood of damaging surround tissue or prosthesis components. Although the procedure is shown using suture fastener 32, the other suture fasteners described herein may alternatively be used.

Although FIGS. 8A-C show the use of a single suture 22 (i.e., mattress suturing), multiple sutures 22 may instead be used, as is known in the art (similar to the approach shown in FIGS. 5A-B.

Surgical fastener system 20 may also be used to fasten any other surgical sutures for any other medical procedure, including, but not limited to, implantation of other valvular prostheses (such an rings, band, or prosthetic valves), including for the mitral, tricuspid, and aortic valves.

Reference is now made to FIGS. 9A-F, which are schematic illustrations of the use of surgical fastener instrument 30 for crimping a single suture fastener 32, in accordance with an application of the present invention. Reference is also made to FIGS. 10A-F, which are schematic illustrations of another use of surgical fastener instrument 30 for crimping a single suture fastener 32, in accordance with an application of the present invention.

In FIGS. 9A and 10A, the one or more sutures 22 are shown prior to being fastened using suture fastener 32. For example, as shown, the one or more sutures 22 may include exactly one suture 22, which has two portions 62A and 62B, which are fastened together by suture fastener 32. Alternatively, two or more sutures 22 are fastened together by suture fastener 32 (configuration not shown). Further alternatively, exactly one portion of exactly one suture 22 is fastened to suture fastener 32 (configuration not shown), for various applications. By way of example and not limitation, the one or more sutures 22 are shown fastening annuloplasty ring 60 to tissue 64 of the mitral valve.

In the use of surgical fastener instrument 30 shown in FIGS. 9A-D, suture portions 62A and 62B are arranged on generally opposite sides of outer delivery tube 36, while in the use of surgical fastener instrument 30 shown in FIGS. 10A-D, suture portions 62A and 62B are arranged on generally the same side of outer delivery tube 36.

For some applications, such as shown in FIGS. 9B and 10B, outer delivery tube 36 is shaped so as to define one or more lateral openings 70 that extend to distal end 40, and facilitate insertion of the one or more portions 62A and 62B of the one or more sutures 22 into outer delivery tube 36 and through the respective portions of suture fastener 32.

For some applications, as shown in FIGS. 9B and 10B and 9C and 10C, surgical fastener instrument 30 is configured such that when suture fastener 32 is removably disposed in outer delivery tube 36 in unlocked conical helical configuration 50, and the one or more portions 62A and 62B of the one or more sutures 22 are disposed partially within outer delivery tube 36, rotation of inner delivery shaft 42 rotates suture fastener 32, thereby causing the one or more portions 62A and 62B of the one or more sutures 22 to pass through the respective portions of suture fastener 32. Typically, the rotation causes the one or more portions 62A and 62B of the one or more sutures 22 to become entangled with the respective portions of suture fastener 32. Generally, additional rotation of suture fastener 32 captures additional suture in the fastener, thereby increasing the tension in the one or more sutures. Controlling the amount of rotations thus allows the surgeon to achieve a desired level of tension in the one or more sutures, such as to avoid loose knots, on the one hand, and overtightening on the other hand.

As shown in FIGS. 9C and 10C, after the one or more portions 62A and 62B of the one or more sutures 22 pass through the respective portions of suture fastener 32, distal end 40 of outer delivery tube 36 is typically pressed tightly against the implant.

As shown in FIGS. 9C-D and 10C-D, surgical fastener instrument 30 is arranged such that the distal advancement of inner delivery shaft 42 transitions suture fastener 32 from unlocked conical helical configuration 50 to locked planar spiral configuration 52 while suture fastener 32 is disposed entirely within outer delivery tube 36. For some applications, surgical fastener instrument 30 is configured to rotate inner delivery shaft 42 during distal advancement of inner delivery shaft 42, such as to facilitate the transition from unlocked conical helical configuration 50 to locked planar spiral configuration 52 illustrated between FIGS. 2A and 2B. For some applications, as shown perhaps most clearly in FIGS. 1, 9B, and 10B, distal end 40 of outer delivery tube 36 is shaped so as to define one or more radially-inwardly-extending lips 72, each of which extends partially around distal opening 38, and which hold suture fastener 32 in outer delivery tube 36 during distal advancement of inner delivery shaft 42 to transition suture fastener 32 from unlocked conical helical configuration 50 to locked planar spiral configuration 52. As a result, surgical fastener instrument 30 does not require a rigid counter-surface to operate properly, i.e., the instrument can operate against a flexible prosthesis. In addition, surgical fastener instrument 30 does not require the one or more sutures to be under high tension during crimping for optimal placement.

This crimping of suture fastener 32 to the one or more sutures 22 tightens the sutures and keeps them in place, maintaining tension in the sutures.

As shown in FIGS. 9E and 10E, after the one or more portions 62A and 62B of the one or more sutures 22 have been fixedly fastened to suture fastener 32, surgical fastener instrument 30, including outer delivery tube 36 and inner delivery shaft 42, is disengaged from suture fastener 32 and the one or more portions 62A and 62B of the one or more sutures 22. For some applications, distal end 40 of outer delivery tube 36 is shaped to allow distal passage of suture fastener 32 out of distal opening 38 when suture fastener 32 is in locked planar spiral configuration 52, as shown in FIGS. 9E and 10E. For some applications, distal end 40 of outer delivery tube 36 is shaped to allow the distal release of suture fastener 32 out of distal opening 38 upon rotation of outer delivery tube 36 with respect to suture fastener 32 when suture fastener 32 is in locked planar spiral configuration 52. This rotation generally aligns the greatest dimension D of suture fastener 32 (labeled in FIG. 2C) with lateral openings 70, and the smallest dimension of suture fastener 32 with lips 72, such that suture fastener 32 can pass out of distal opening 38.

As mentioned above, in the use of surgical fastener instrument 30 shown in FIGS. 9A-D, suture portions 62A and 62B are arranged on generally opposite sides of outer delivery tube 36, while in the use of surgical fastener instrument 30 shown in FIGS. 10A-D, suture portions 62A and 62B are arranged on generally the same side of outer delivery tube 36. As a result, after use of surgical fastener instrument 30 as shown in FIGS. 9E-F, suture portions 62A and 62B are arranged on generally opposite sides of suture fastener 32, while after use of surgical fastener instrument 30 as shown in FIGS. 10E-F, suture portions 62A and 62B are arranged on generally the same side of suture fastener 32. Optionally, this arrangement allows both suture portions 62A and 62B to pass through an innermost turn of the spiral.

Of course, suture portions 62A and 62B may be arranged at other relative angular positions with respect to each other, such as offset at an angle of between 1 and 180 degrees about a center of suture fastener 32, e.g., between 45 and 135 degrees, such as 90 degrees.

Figure 11A:
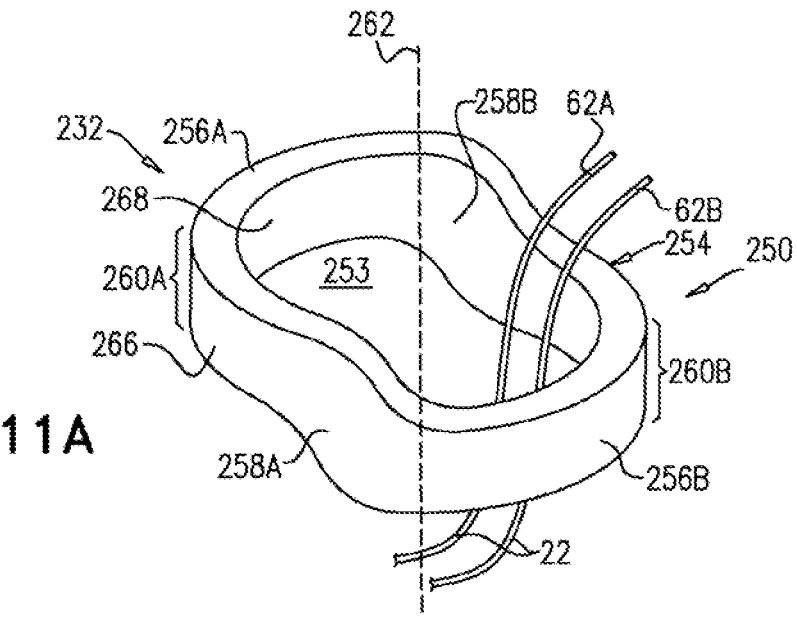
FIGS. 11A-F are schematic illustrations of another suture fastener, in accordance with an application of the present invention.
Figure 11B:
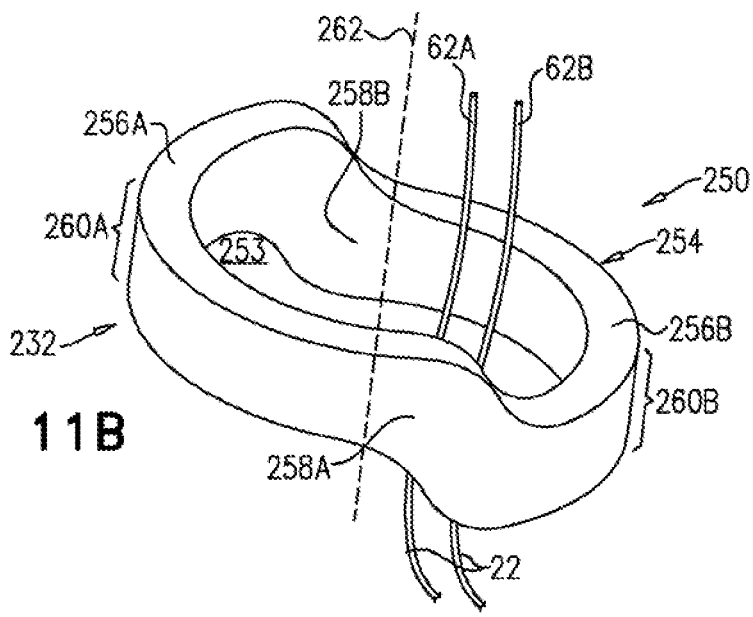
Figure 11C:
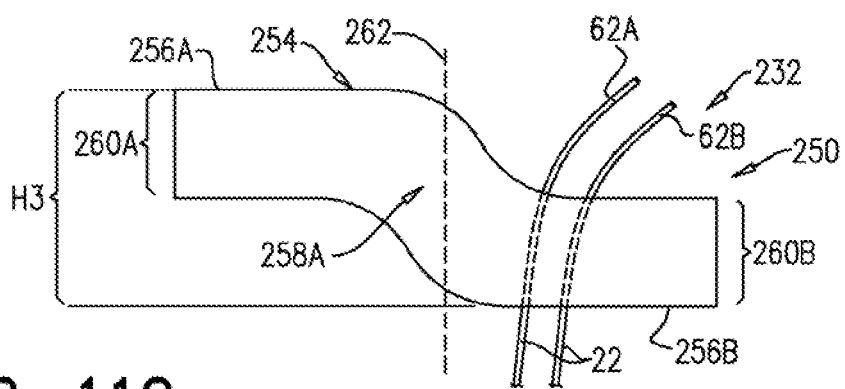
Figure 11D:
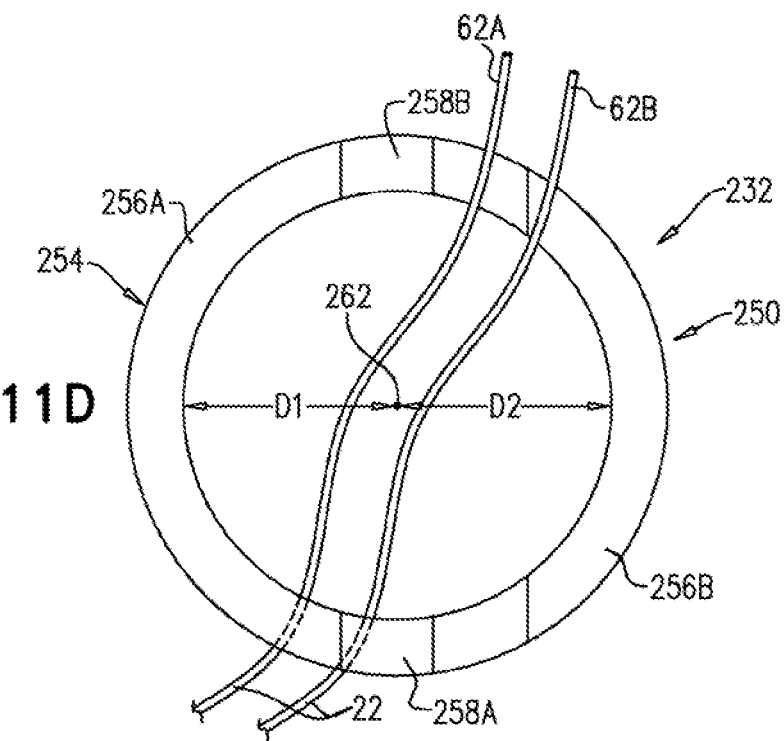
Figure 11E:
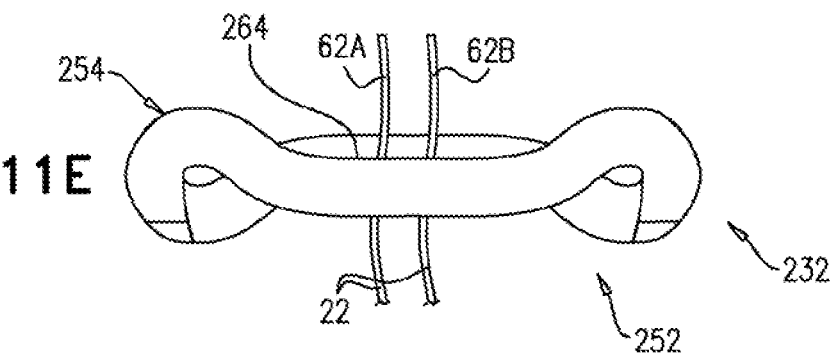
Figure 11F:
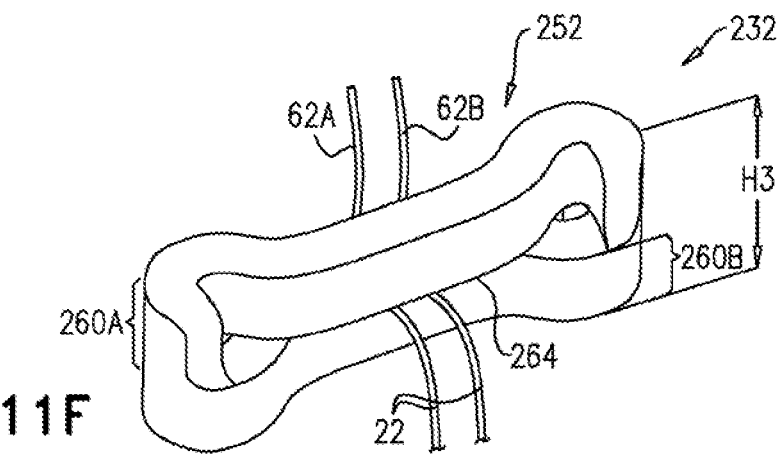

Reference is now made to FIGS. 11A-F, which are schematic illustrations of a suture fastener 232, in accordance with an application of the present invention. In FIGS. 11A-D, suture fastener 232 is shown in unlocked open configuration 250. In FIGS. 11E-F, suture fastener 232 is shown in locked closed configuration 252. FIGS. 11A-F also show a suture 22, which is positioned within a central opening 253 of suture fastener 232, such as by hooking or positioning manually. Suture 22 is typically not elements of the suture fastener or the surgical fastener system. Suture fastener 232 may implement any of the features of suture fastener 32 described hereinabove, mutatis mutandis, including, but not limited to, its resting state (e.g., in the unlocked open configuration), material properties, and plasticity.

As shown in FIGS. 11A-D, when in unlocked open configuration 250, suture fastener 232 is shaped so as to define a continuous loop 254 that is shaped so as to define central opening 253 surrounded by continuous loop 254. Continuous loop 254 includes first and second crimping portions 256A and 256B, which are joined to each other at first and second joining portions 258A and 258B (such that the portions are arranged around continuous loop 254 in the following order: first crimping portion 256A, first joining portion 258A, second crimping portion 256B, second joining portion 258B). First and second crimping portions 256A and 256B are disposed at different first and second axial locations 260A and 260B, respectively, along a central longitudinal axis 262 defined by continuous loop 254 and passing through central opening 253. When suture fastener 232 is disposed in an outer delivery tube of a surgical fastener instrument, central longitudinal axis 262 is also defined by the outer delivery tube.

It is noted that first and second crimping portions 256A and 256B are not merely arbitrary portions of a completely cylindrical piece of material. Instead, suture fastener 232 does not comprise any material at the circumferential location of first crimping portion 256A, other than at first axial location 260A, and suture fastener 232 does not comprise any material at the circumferential location of second crimping portion 256B, other than at second axial location 260B. By "circumferential location" it is meant the angular position around central longitudinal axis 262.

For some applications, when suture fastener 232 is in unlocked open configuration 250:
central longitudinal axis 262 is parallel to an outer surface 266 of continuous loop 254 facing away from central longitudinal axis 262, and/or
central longitudinal axis 262 is parallel to an inner surface 268 of continuous loop 254 facing toward central longitudinal axis 262.

For some applications, when suture fastener 232 is in unlocked open configuration 250, each of first and second crimping portions 256A and 256B defines a portion of a cylinder, e.g., is generally half-cylindrical, such as shown in FIGS. 11A-D.

For some applications, when suture fastener 232 is in unlocked open configuration 250, the different first and second axial locations 260A and 260B at which first and second crimping portions 256A and 256B are respectively disposed do not axially overlap (as shown in FIGS. 11A-D) or axially overlap by less than 1 mm. The phrase "axially overlap" means axially coincide, i.e., be disposed at some of the same axial positions along central longitudinal axis 262.

For some applications, when suture fastener 232 is in unlocked open configuration 250, an average distance D1 of first crimping portion 256A from central longitudinal axis 262 equals between 75% and 125%, e.g., between 95% and 105%, such as 100%, of an average distance D2 of second crimping portion 256B from central longitudinal axis 262.

For some applications, both when suture fastener 232 is in unlocked open configuration 250 and when suture fastener 232 is in locked closed configuration 252, a height H3, measured along central longitudinal axis 262, is at least 1 mm and/or less than 20 mm, e.g., less than 7 mm, such as less than 5 mm, such as less than 4 mm, e.g., less than 3 mm. Typically, the height H3 of suture fastener 232 when in unlocked open configuration 250 equals the height H3 of suture fastener 232 when in locked closed configuration 252. Typically, respective heights of first and second crimping portions 256A and 256B equal each other and/or equal half of height H3.

As shown in FIGS. 11E-F, when suture fastener 232 is in locked closed configuration 252, a contact interface 264 between first and second crimping portions 256A and 256B creates friction that prevents sliding of the one or more sutures 22, thereby fastening the suture portions or sutures together. For example, contact interface 264 may include a straight portion, or may be entirely straight. Typically, in order to transition suture fastener 232 from unlocked open configuration 250 to locked closed configuration 252, a lateral crimping force is applied to at least one of first and second crimping portions 256A and 256B of suture fastener 232, such as using a surgical fastener instrument similar to surgical fastener instrument 30, described hereinabove. The lateral crimping force transitions suture fastener 232 from unlocked open configuration 250 to locked closed configuration 252, in which the one or more sutures 22 are fixedly crimped and coupled to suture fastener 232. Typically, the lateral crimping force is perpendicular to central longitudinal axis 262.

For some applications, the lateral crimping force is applied to both first and second crimping portions 256A and 256B of suture fastener 232. For other applications, the lateral crimping force is applied to only one of first and second crimping portions 256A and 256B, while the other crimping portion is held relatively stationary by the surgical fastener instrument, until the force applied to the one crimping portion transitions the suture fastener 232 to locked closed configuration 252.

As shown in FIGS. 11A-D, when the suture fastener 232 is unlocked open configuration, one or more sutures 22 are positioned within the central opening 253. The positioning of the suture 22 is aided by means of standard surgical instruments (e.g. surgical forceps) or by positioning tools integrated within the delivery system. In some embodiment an hook is passed through the central lumen 253, to engage the suture 22 in the distal groove of the hook at the opposite direction that the hook entrance into the central lumen 253, that then is positioned within and across the opening 253 by retraction of the hook. In another embodiment a metallic suture loop is passes through the opening 253, to open and expand its loop. The suture 22 is passes through this loop opening and is positioned through the central opening 253 by exiting the loop within the opening, then to free the suture 22 that will remain at the edge across the opening 253. Once the suture 22 is positioned within the opening 253 the fastener is crimped and excessive suture is cut.

Figure 12A:
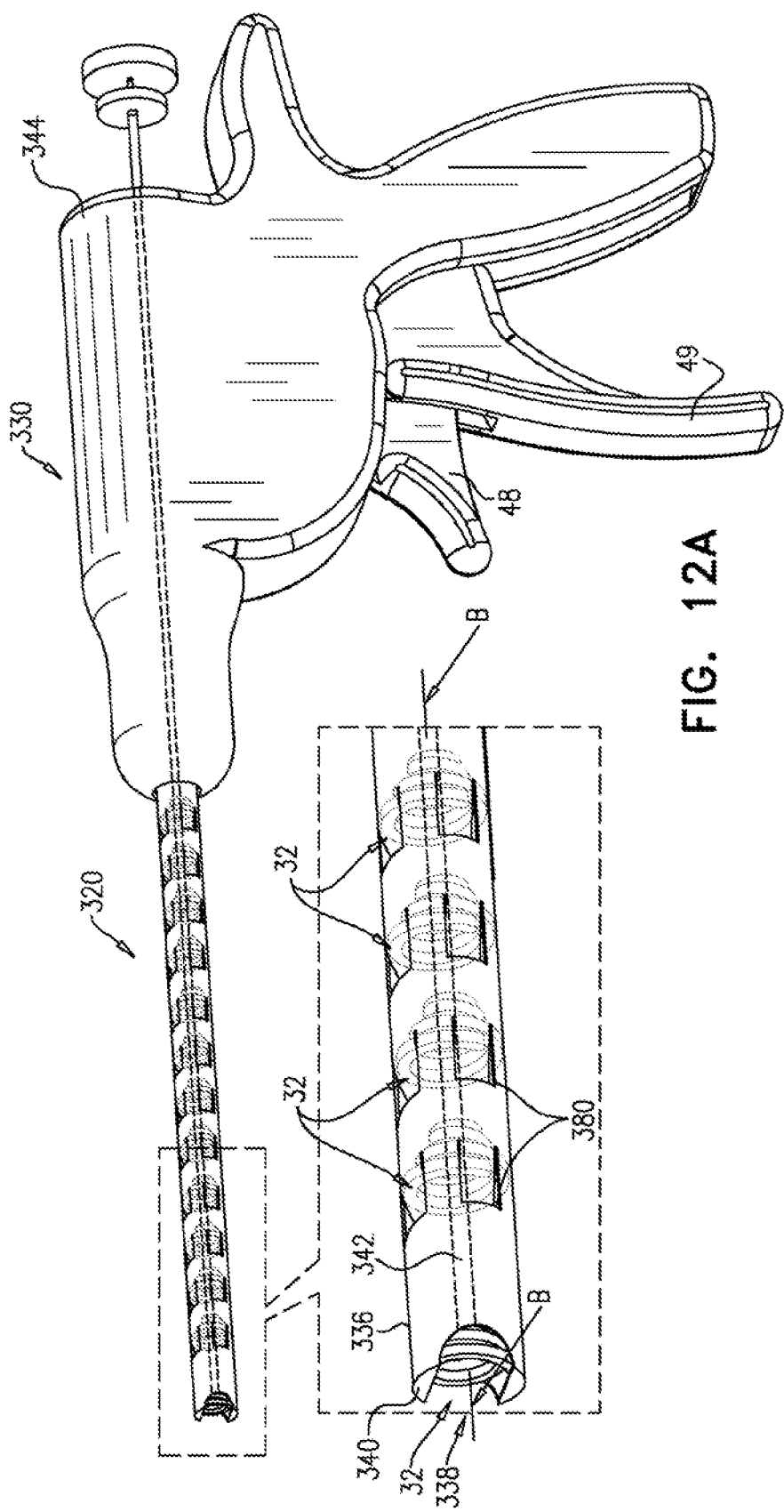
FIGS. 12A-C are schematic illustrations of another surgical fastener system for fastening one or more sutures, in accordance with an application of the present invention.
Figure 12B:
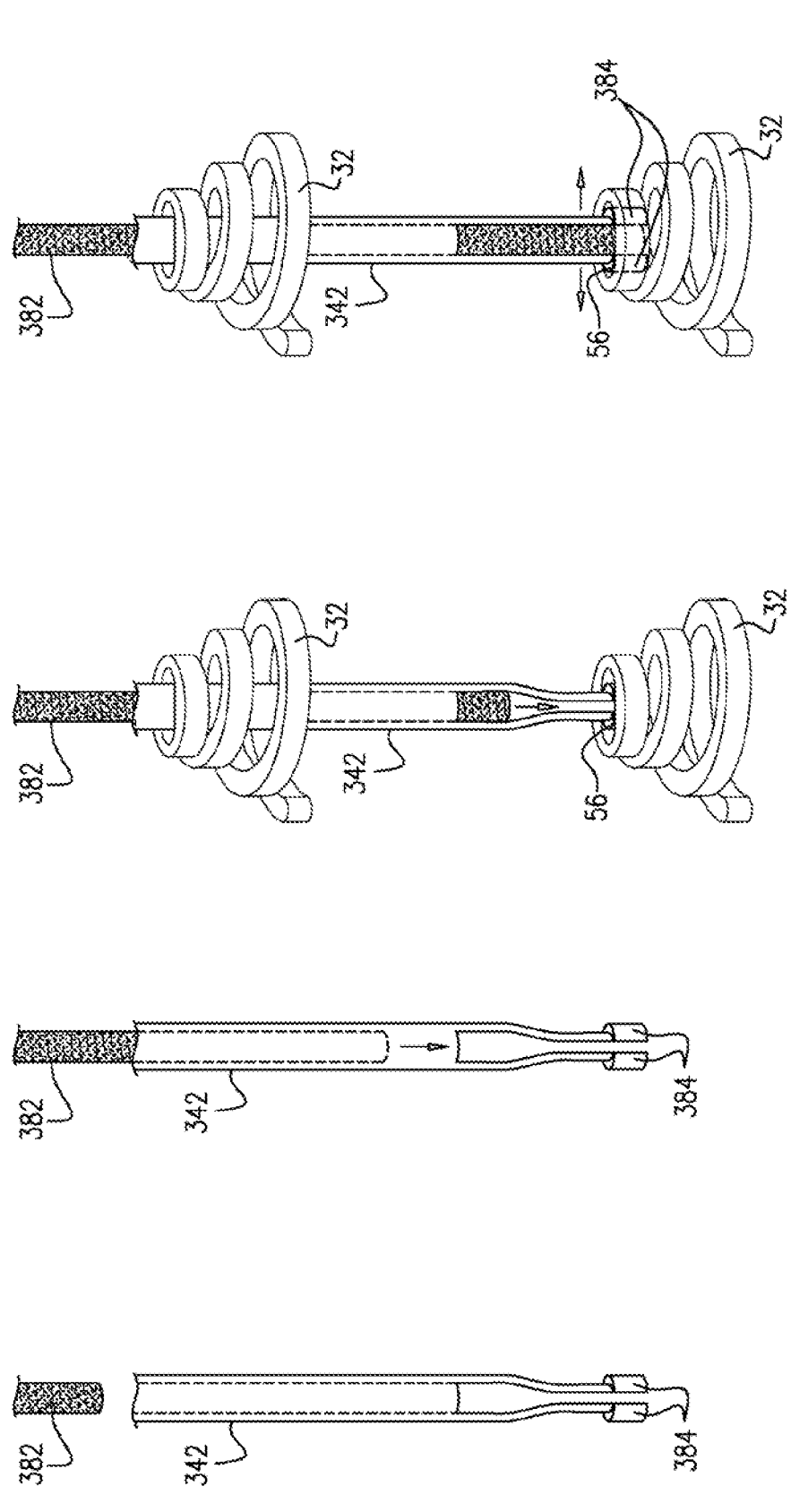
Figure 12C:
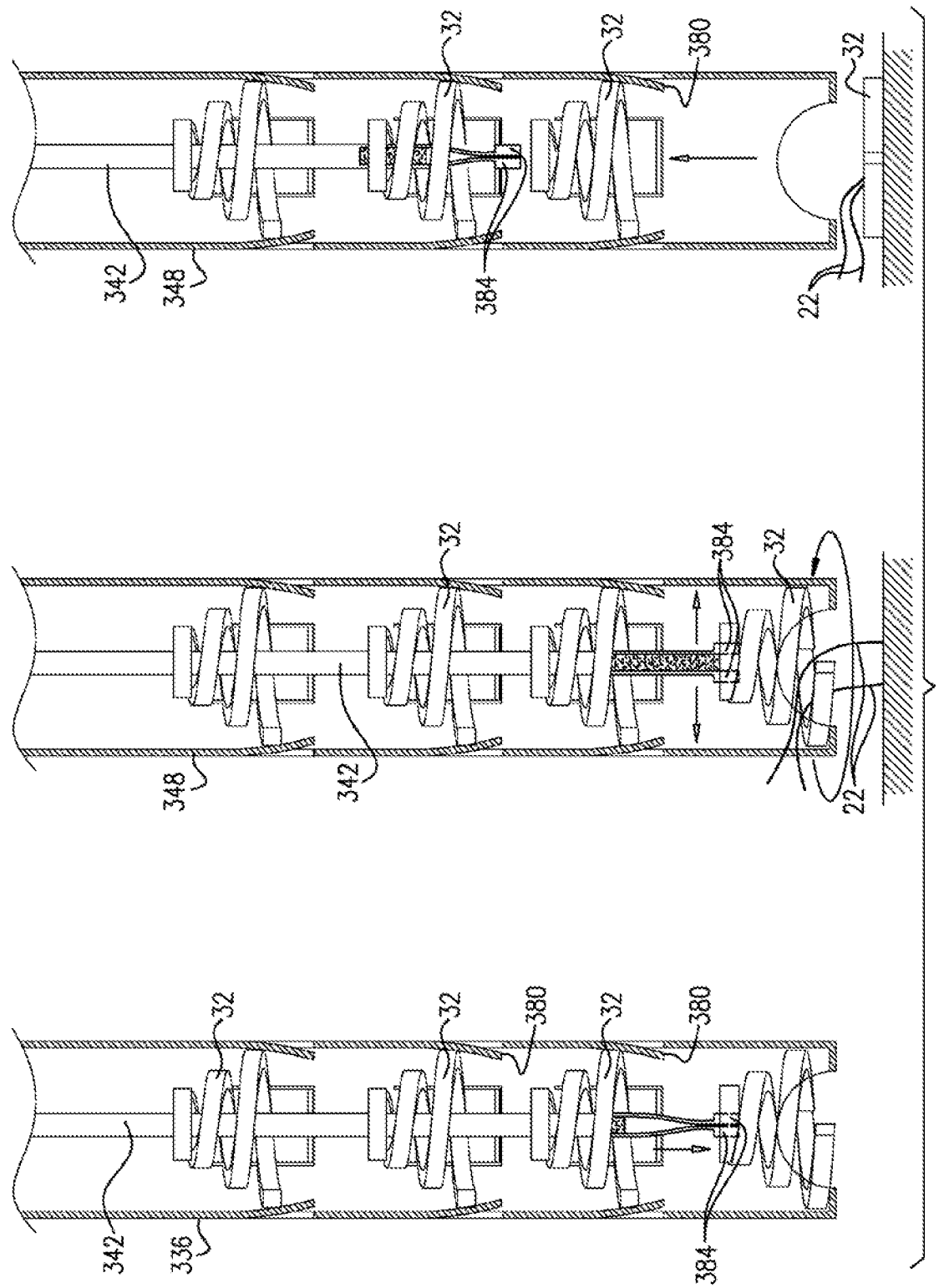

FIGS. 12A-C are schematic illustrations of a surgical fastener system 320 for fastening one or more sutures 22, in accordance with an application of the present invention. The one or more sutures 22 shown in FIG. 12C are typically not elements of surgical fastener system 320. Other than described below, surgical fastener system 320 is similar to surgical fastener system 20, described hereinabove with reference to FIGS. 1, 9A-F, and 10A-F, and may implement any of the features thereof, mutatis mutandis. Although surgical fastener system 320 is described with reference to suture fasteners 32, the system may alternatively deploy a plurality of the other suture fasteners described herein, mutatis mutandis.

Surgical fastener system 320 comprises a surgical fastener instrument 330 and a plurality of suture fasteners 32 (e.g., between 2 and 25 suture fasteners 32. Surgical fastener instrument 330 comprises:
- an outer delivery tube 336, which has a distal opening 338 at a distal end 340 of outer delivery tube 336;
- an inner delivery shaft 342, which is disposed at least partially in outer delivery tube 336; and
- a handle 344, which is coupled to a proximal portion of outer delivery tube 336, and comprises a user control element 48, e.g., a knob, trigger, or button, arranged to rotate inner delivery shaft 342 with respect to outer delivery tube 336.

A plurality of suture fasteners 32 are contained with outer delivery tube 336, typically with inner delivery shaft 342 passing through suture fasteners 32. Outer delivery tube 336 thus functions as a multiple-fastener cartridge, which enables the deployment of multiple suture fasteners 32 and allows for fast and quick application of surgical fastener instrument 330 on sutures 22 without requiring from the operator to manually reapply the surgical fastener instrument for the deployment of each suture fastener 32 separately.

Typically, user control element 48 is operated by the palm and fingers of the operator using wrist and finger movement, using little force. For some applications, handle 344 comprises a plurality of user control elements 48, for controlling the different functions of surgical fastener instrument 330 during the several steps of its use, as described hereinbelow with reference to FIGS. 12B-C. For example, user control element 48 may be a first user control element 48, and handle 344 may comprise a second user control element 49, which is arranged to cause distal advancement of inner delivery shaft 342 (typically with respect to outer delivery tube 336).

For some applications, outer delivery tube 336 is shaped so as to define a plurality of tabs 380, which are biased radially inward, and are configured to temporarily hold suture fasteners 32, respectively, in place within the outer delivery tube until the fasteners are individually axially advanced and deployed.

For some applications, as shown in FIGS. 12B and 12C, in order to advance a single suture fastener 32 at a time, surgical fastener instrument 330 is configured to cause inner delivery shaft 342 to move axially in order to engage each of suture fasteners 32 one at a time, beginning with the distal-most fastener and working proximally as each fastener is deployed. Optionally, this action is automated within surgical fastener instrument 330 using a spring and a knob, to avoid to activity work on inner delivery shaft 342 to free the previous fastener and connect to the next in the cartridge.

For some of these applications, in order to advance a single suture fastener 32 at a time, inner delivery shaft 342 is shaped so as to define two distal prongs 384. When distal prongs 384 are disposed in a radially compressed configuration, such as shown in the three left-most figures in FIG. 12B and the left-most figure in FIG. 12C, the distal prongs can pass through the non-circular and non-spiral openings 56 of suture fasteners 32. Once distal prongs 384 are inserted in the distal-most suture fastener 32 (i.e., the lowest suture fastener 32 in FIGS. 12B and 12C), the distal prongs are radially expanded, such as by inserting an inner shaft 382, and the distal prongs engage opening 56 of the distal-most suture fastener 32. This distal-most suture fastener is rotated and axially compressed, such as described hereinabove regarding surgical fastener instrument 30 with reference to FIG. 1. For some applications, the advancement and withdrawal of inner shaft 382 with respect to inner delivery shaft 342 is controlled by separate user control elements, e.g., respective concentric control elements, as shown, while for other applications, one or first or second user control elements 48 or 49 also controls the advancement and withdrawal of inner shaft 382 with respect to inner delivery shaft 342 (configuration not shown).

As shown in FIG. 12C, surgical fastener instrument 30 is used in the same manner as surgical fastener instrument 30, described hereinabove with reference to FIG. 1, for completing the locking and deployment of each suture fastener 32, mutatis mutandis.

Figure 13A:
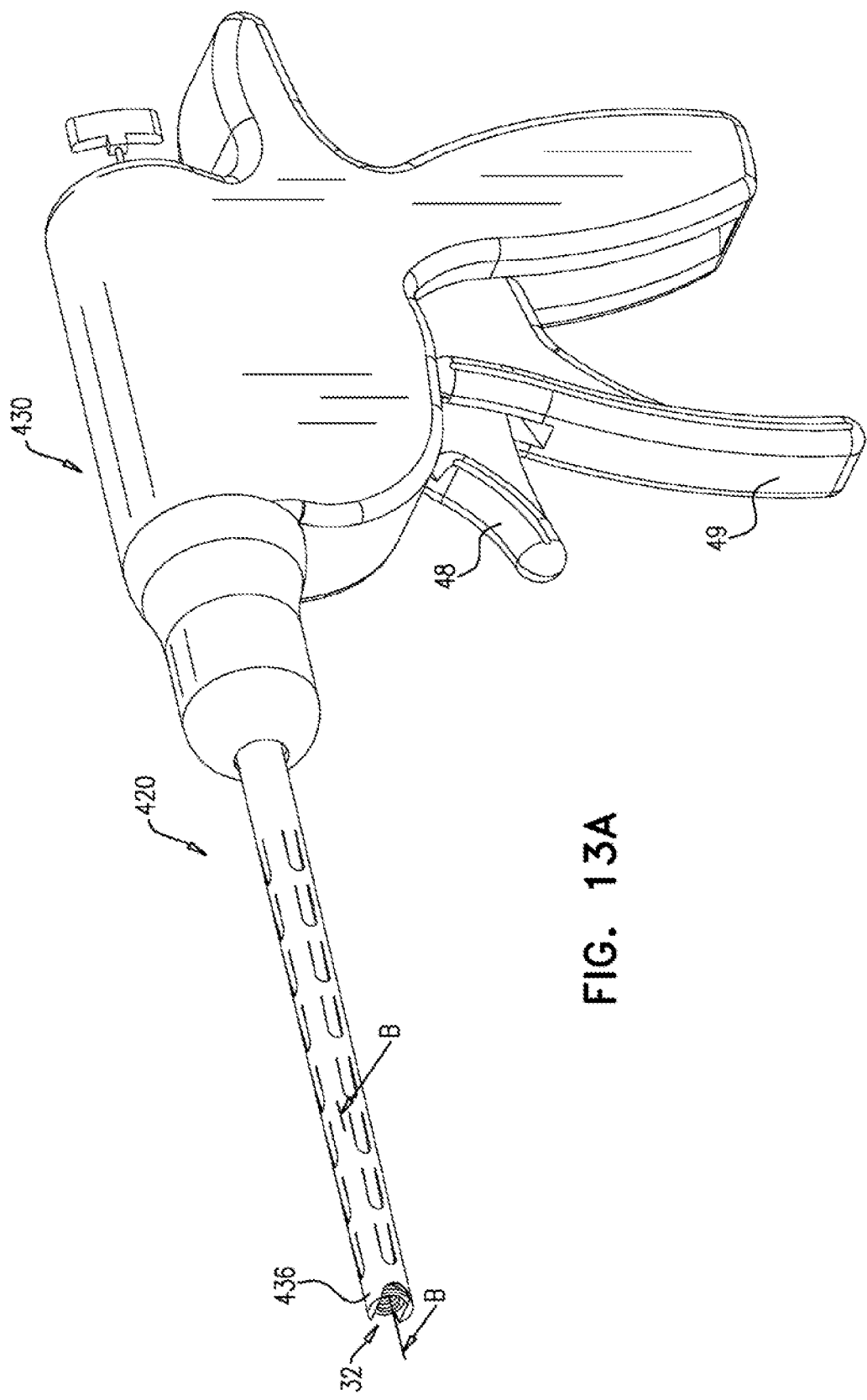
FIGS. 13A-B are schematic illustrations of yet another surgical fastener system for fastening one or more sutures, in accordance with an application of the present invention.
Figure 13B:
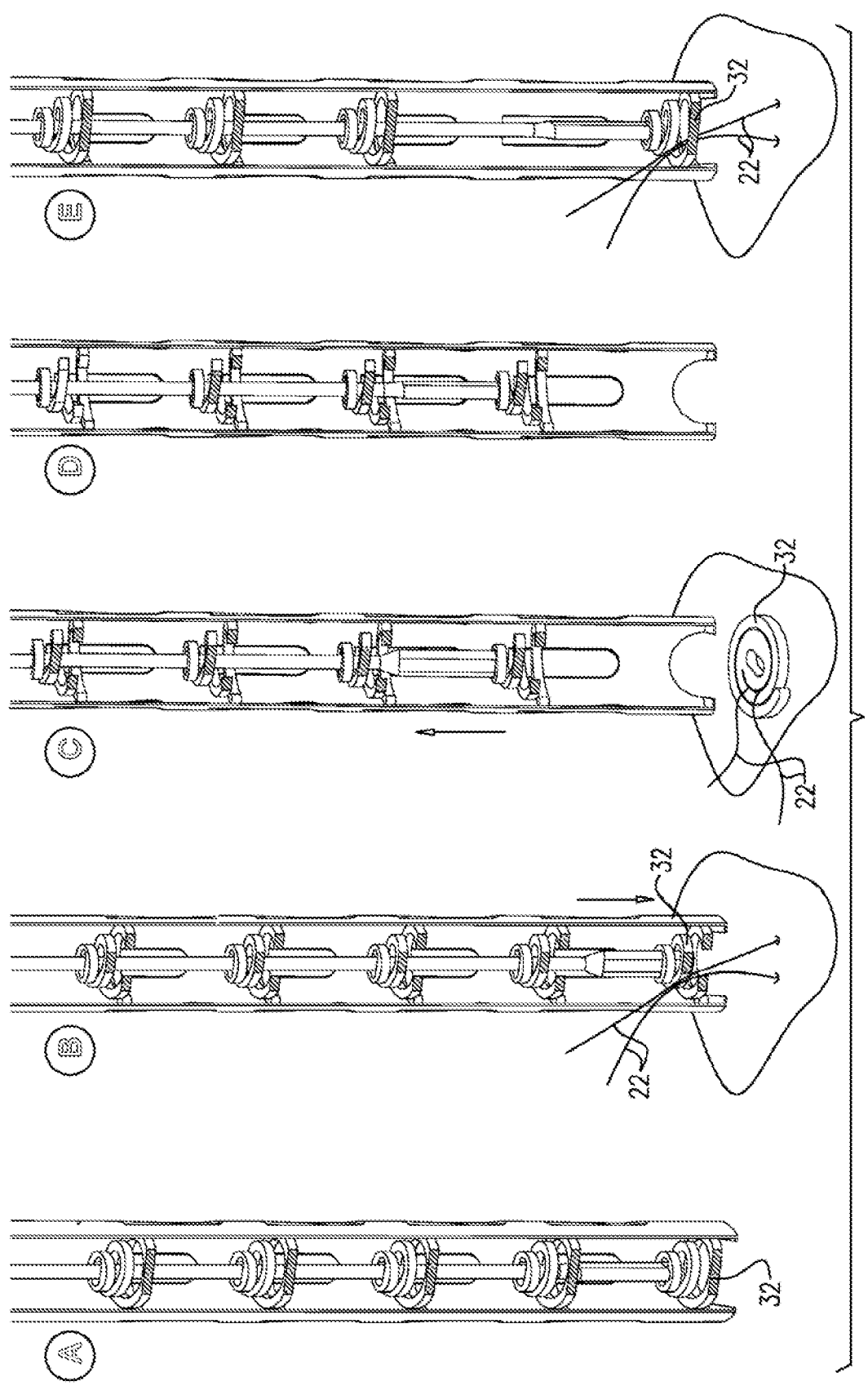

FIGS. 13A-B are schematic illustrations of a surgical fastener system 420 for fastening one or more sutures 22, in accordance with an application of the present invention. The one or more sutures 22 shown in FIG. 13B are typically not elements of surgical fastener system 420. Other than described below, surgical fastener system 420 is similar to surgical fastener system 320, described hereinabove with reference to FIGS. 12A-C, and may implement any of the features thereof, mutatis mutandis. Surgical fastener system 420 comprises a surgical fastener instrument 430 and a plurality of suture fasteners 32 (e.g., between 2 and 16 suture fasteners 32). Although surgical fastener system 420 is described with reference to suture fasteners 32, the system may alternatively deploy a plurality of the other suture fasteners described herein, mutatis mutandis. Typically, rotation of inner delivery shaft 342, e.g., by 90 degrees, engage/disengages each suture fastener 32. For some applications, the rotation of inner delivery shaft 342 is controlled by separate user control elements, as shown, while for other applications, one or first or second user control elements 48 or 49 also controls the rotation of inner delivery shaft 342 (configuration not shown).

Figure 14:
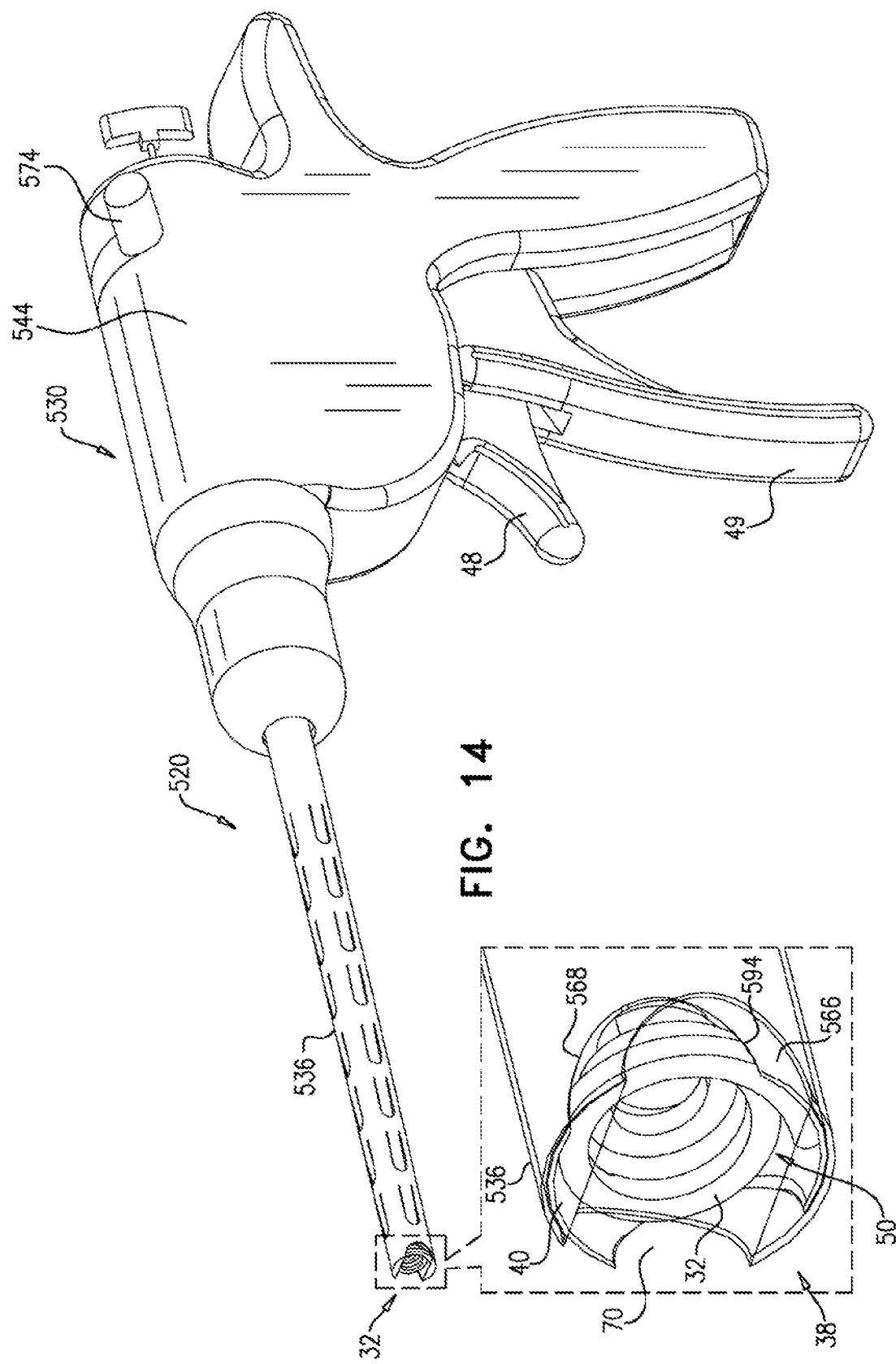
FIG. 14 is a schematic illustration of still another surgical fastener system for fastening one or more sutures, in accordance with an application of the present invention.

Reference is now made to FIG. 14, which is a schematic illustration of a surgical fastener system 520 for fastening one or more sutures 22, in accordance with an application of the present invention. The one or more sutures 22 are typically not elements of surgical fastener system 520. Other than described below, surgical fastener system 520 is similar to surgical fastener system 20, described hereinabove with reference to FIGS. 1, 9A-F, and 10A-F, and may implement any of the features thereof, and/or of surgical fastener system 320, described hereinabove with reference to FIGS. 12A-C, and/or of surgical fastener system 420, described hereinabove with reference to FIGS. 13A-B, mulalis mutandis. Although surgical fastener system 520 is described with reference to suture fasteners 32, the system may alternatively deploy a plurality of the other suture fasteners described herein, mutatis mutandis.

A surgical fastener instrument 530 of surgical fastener system 520 further comprises one or more blades 594 (e.g., exactly one blade 594), which are configured to cut the one or more sutures 22. For some applications, surgical fastener system 520 further comprises a cutting shaft 566, which is shaped so as to define the one or more blades 594. For example, a distal portion of cutting shaft 566 may be shaped so as to define the one or more blades 594; optionally the distal portion is shaped so as to define one or more scallops 568, which arc shaped so as to define the one or more blades 594.

The rotation of cutting shaft 566 cuts the one or more sutures 22 by applying the cutting force of the one or more blades 594 against the one of more sutures 22, which are held in position during the rotation by the boundary of lateral opening 70 of an outer delivery tube 536 of surgical fastener system 520.

For some applications, handle 544 comprises a separate third user control element 574, which is arranged to cause the rotation of cutting shaft 566.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A surgical fastener system for fastening one or more sutures, the surgical fastener system comprising:
   (a) a surgical fastener instrument, which comprises:
      an outer delivery tube, which has a distal opening at a distal end of the outer delivery tube;
      an inner delivery shaft, which is disposed at least partially in the outer delivery tube; and
      a handle, which is coupled to a proximal portion of the outer delivery tube, and comprises a user control element arranged to rotate the inner delivery shaft with respect to the outer delivery tube; and
   (b) a suture fastener, which is removably disposed in the outer delivery tube in an unlocked conical helical configuration,
   wherein the surgical fastener instrument is arranged such that distal advancement of the inner delivery shaft, when one or more portions of the one or more sutures pass through respective portions of the suture fastener, transitions the suture fastener from the unlocked conical helical configuration to a locked planar spiral configuration, in which the one or more sutures are fixedly coupled to the suture fastener,
   wherein the outer delivery tube is shaped so as to define one or more lateral openings that extend to the distal end, and facilitate insertion of the one or more portions of the one or more sutures into the outer delivery tube and through the respective portions of the suture fastener, and
   wherein the surgical fastener instrument is configured such that when the suture fastener is removably disposed in the outer delivery tube in the unlocked conical helical configuration, and the one or more sutures are disposed partially within the outer delivery tube;

rotation of the inner delivery shaft rotates the suture fastener, thereby causing the one or more portions of the one or more sutures to pass through the respective portions of the suture fastener.

2. The surgical fastener system according to claim 1, wherein the suture fastener is configured to assume the unlocked conical helical configuration when in a resting state, and wherein the surgical fastener instrument is arranged such that the distal advancement of the inner delivery shaft transitions the suture fastener from the unlocked conical helical configuration to the locked planar spiral configuration by axially plastically deforming the suture fastener.

3. The surgical fastener system according to claim 1, wherein a height of the suture fastener, when in the locked planar spiral configuration, is less than 5 mm.

4. The surgical fastener system according to claim 1, wherein the surgical fastener instrument further comprises one or more blades, which are configured to cut the one or more sutures.

5. The surgical fastener system according to claim 1, wherein the suture fastener is shaped as a double helix in the unlocked conical helical configuration, and a double planar spiral in the locked planar spiral configuration.

6. The surgical fastener system according to claim 1, wherein the user control element is a first user control element, wherein the handle comprises a second user control element, which is arranged to cause the distal advancement of the inner delivery shaft, wherein the surgical fastener instrument further comprises one or more blades, which are configured to cut the one or more sutures, and wherein the second user control element is arranged to cause the distal advancement of the inner delivery shaft, and thereafter to cause the one or more blades to cut the one or more sutures.

7. The surgical fastener system according to claim 1, wherein the user control element is arranged to both rotate the inner delivery shaft with respect to the outer delivery tube and to cause the distal advancement of the inner delivery shaft.

8. The surgical fastener system according to claim 1, wherein the surgical fastener instrument is arranged such that the distal advancement of the inner delivery shaft transitions the suture fastener from the unlocked conical helical configuration to the locked planar spiral configuration while the suture fastener is disposed entirely within the outer delivery tube.

9. The surgical fastener system according to claim 8, wherein the distal end of the outer delivery tube is shaped so as to define one or more radially-inwardly-extending lips, each of which extends partially around the distal opening, and which hold the suture fastener in the outer delivery tube during distal advancement of the inner delivery shaft to transition the suture fastener from the unlocked conical helical configuration to the locked planar spiral configuration.

10. The surgical fastener system according to claim 1, wherein the surgical fastener instrument is configured such that the rotation of the inner delivery shaft rotates the suture fastener, thereby causing the one or more portions of the one or more sutures to become entangled with the respective portions of the suture fastener.

11. The surgical fastener system according to claim 1, wherein the distal end of the outer delivery tube is shaped to allow distal passage of the suture fastener out of the distal opening when the suture fastener is in the locked planar spiral configuration.

12. The surgical fastener system according to claim 1, wherein the suture fastener is shaped so as to define a spiral portion, which is (a) conically helical when the suture fastener is in the unlocked conical helical configuration and (b) planar spiral when the suture fastener is in the planar spiral configuration, and wherein the suture fastener is shaped so as to define a radially-inward portion that, both when the suture fastener is in the unlocked conical helical configuration and when the suture fastener is in the locked planar spiral configuration, (a) is neither helical nor spiral, and (b) is disposed radially inward from the spiral portion.

13. The surgical fastener system according to claim 12, wherein the radially-inward portion is shaped so as to define a non-circular and non-spiral opening, and wherein a distal end of the inner delivery shaft is shaped so as to engage the non-circular and non-spiral opening.

14. The surgical fastener system according to claim 1, wherein the surgical fastener system comprises a plurality of suture fasteners, which are removably disposed in the outer delivery tube, each in an unlocked conical helical configuration.

15. A method for fastening one or more sutures, the method comprising:

providing a surgical fastener system including:
(a) a surgical fastener instrument, which includes:
an outer delivery tube, which (i) has a distal opening at a distal end of the outer delivery tube, and (ii) is shaped so as to define one or more lateral openings that extend to the distal end and facilitate insertion of one or more portions of the one or more sutures into the outer delivery tube and through respective portions of the suture fastener;
an inner delivery shaft, which is disposed at least partially in the outer delivery tube; and
a handle, which is coupled to a proximal portion of the outer delivery tube, and includes a user control element arranged to rotate the inner delivery shaft with respect to the outer delivery tube; and
(b) a suture fastener, which is removably disposed in the outer delivery tube in an unlocked conical helical configuration;

inserting the one or more sutures partially within the outer delivery tube using the one or more lateral openings;

rotating the suture fastener by rotating the inner delivery shaft, thereby causing the one or more portions of the one or more sutures to pass through the respective portions of the suture fastener while (a) the suture fastener is in the unlocked conical helical configuration removably disposed in the outer delivery tube, and (b) the one or more sutures are disposed partially within the outer delivery tube; and transitioning the suture fastener from the unlocked conical helical configuration to a locked planar spiral configuration, in which the one or more sutures are fixedly coupled to the suture fastener, by distally advancing the inner delivery shaft when the one or more portions of the one or more sutures pass through the respective portions of the suture fastener.

16. The method according to claim 15, wherein the suture fastener is configured to assume the unlocked conical helical configuration when in a resting state, and wherein transitioning the suture fastener from the unlocked conical helical configuration to the locked planar spiral configuration includes axially plastically deforming the suture fastener.

17. The method according to claim 15, wherein passing the one or more portions of the one or more sutures through respective portions of the suture fastener includes entangling the one or more portions of the one or more sutures with the respective portions of the suture fastener.

18. The method according to claim 15, wherein a height of the suture fastener, when in the locked planar spiral configuration, is less than 5 mm.

19. The method according to claim 15,
wherein the suture fastener is shaped so as to define a spiral portion, which is (a) conically helical when the suture fastener is in the unlocked conical helical configuration and (b) planar spiral when the suture fastener is in the planar spiral configuration, and
wherein the suture fastener is shaped so as to define a radially-inward portion that, both when the suture fastener is in the unlocked conical helical configuration and when the suture fastener is in the locked planar spiral configuration, (a) is neither helical nor spiral, and (b) is disposed radially inward from the spiral portion.

20. The method according to claim 19, wherein the radially-inward portion is shaped so as to define a non-circular and non-spiral opening.

21. The method according to claim 15, wherein transitioning the suture fastener from the unlocked conical helical configuration to the locked planar spiral configuration comprises distally advancing the inner delivery shaft while the suture fastener is disposed entirely within the outer delivery tube.

22. The method according to claim 21, wherein the distal end of the outer delivery tube is shaped so as to define one or more radially-inwardly-extending lips, each of which extends partially around the distal opening, and which hold the suture fastener in the outer delivery tube during the distally advancing of the inner delivery shaft to transition the suture fastener from the unlocked conical helical configuration to the locked planar spiral configuration.

\* \* \* \* \*